US010548966B2

(12) United States Patent
Martinez-Sobrido et al.

(10) Patent No.: US 10,548,966 B2
(45) Date of Patent: Feb. 4, 2020

(54) SINGLE-CYCLE VIRUS FOR THE DEVELOPMENT OF CANINE INFLUENZA VACCINES

(71) Applicants: University of Rochester, Rochester, NY (US); Cornell University, Ithaca, NY (US)

(72) Inventors: Luis Martinez-Sobrido, Rochester, NY (US); Aitor Nogales-Gonzalez, Rochester, NY (US); Colin Parrish, Ithaca, NY (US)

(73) Assignees: UNIVERSITY OF ROCHESTER, Rochester, NY (US); CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/753,688

(22) PCT Filed: Aug. 19, 2016

(86) PCT No.: PCT/US2016/047726
§ 371 (c)(1),
(2) Date: Feb. 20, 2018

(87) PCT Pub. No.: WO2017/031408
PCT Pub. Date: Feb. 23, 2017

(65) Prior Publication Data
US 2018/0256703 A1 Sep. 13, 2018

Related U.S. Application Data

(60) Provisional application No. 62/207,579, filed on Aug. 20, 2015.

(51) Int. Cl.
*A61K 39/145* (2006.01)
*A61P 31/16* (2006.01)
*C12N 7/00* (2006.01)
*A61K 39/00* (2006.01)

(52) U.S. Cl.
CPC ............ *A61K 39/145* (2013.01); *A61P 31/16* (2018.01); *C12N 7/00* (2013.01); *A61K 2039/525* (2013.01); *A61K 2039/552* (2013.01); *C12N 2760/16121* (2013.01); *C12N 2760/16134* (2013.01)

(58) Field of Classification Search
None
See application file for complete search history.

(56) References Cited

U.S. PATENT DOCUMENTS

| 7,722,884 B2* | 5/2010 | Shields ................ A61K 39/145 424/184.1 |
| 2011/0150912 A1 | 6/2011 | Perez |
| 2018/0243401 A1 | 8/2018 | Martinez-Sobrido et al. |
| 2018/0256703 A1* | 9/2018 | Martinez-Sobrido ........................ A61K 39/145 |

FOREIGN PATENT DOCUMENTS

WO 2011/044561 A1 4/2011

OTHER PUBLICATIONS

Voorhees et al. (Emerging Infectious Diseases. Dec. 2017; 23 (12): 1950-1957).*
Hanson et al. ("Canine Influenza" Sep. 2016; Clinicians Brief, University of Georgia: 97-103).*
Guo et al. (Journal of Virology. published online Aug. 6, 2014; 88 (20): 12006-12016).*
Chao (Journal of Biological Chemistry. 1992; 267 (4): 2142-2148).*
Xu et al. (PLoSOne. Jul. 2012; 7 (7): e38665).*
Worobey et al. (Nature. Apr. 2014; 508 (7495): 254).*
Baker et al., 2015, "Downregulating viral gene expression: codon usage bias manipulation for the generation of novel Influenza A virus vaccines." Future Virology, 10: 715-730.
Varghese et al., 1992, "The structure of the complex between influenza virus neuraminidase and sialic acid, the viral receptor." Proteins, 14: -327-332.
Crawford et al., 2005, "Transmission of equine influenza virus to dogs." Science, 310: 482-485.
Song et al., 2008, "Transmission of avian influenza virus (H3N2) to dogs." Emerging Infectious Diseases, 14: 741-746.
JAVMA News. 2015. Outbreak of canine influenza caused by new strain of virus. J Am Vet Med Assoc. 246:1049-1049.
Jeoung et al., 2013, "A novel canine influenza H3N2 virus isolated from cats in an animal shelter." Veterinary Microbiology, 165: 281-286.
Song et al., 2011, "Interspecies transmission of the canine influenza H3N2 virus to domestic cats in South Korea, 2010." The Journal of General Virology, 92: 2350-2355.
Yoon et al., 2005, "Influenza virus infection in racing greyhounds." Emerging Infectious Diseases, 11: 1974-1976.
Holt et al., 2010, "Serologic prevalence of antibodies against canine influenza virus (H3N8) in dogs in a metropolitan animal shelter." Journal of the American Veterinary Medical Association, 237: 71-73.
Pecoraro et al., 2013, "Evaluation of virus isolation, one-step real-time reverse transcription polymerase chain reaction assay, and two rapid influenza diagnostic tests for detecting canine Influenza A virus H3N8 shedding in dogs." Journal of Veterinary Diagnostic Investigation, 25: 402-406.
Gonzalez et al., 2014, "Infection and pathogenesis of canine, equine, and human influenza viruses in canine tracheas." J Virol, 88: 9208-9219.
Song et al., 2015, "Canine susceptibility to human influenza viruses (A/pdm 09H1N1, A/H3N2 and B)." The Journal of General Virology, 96: 254-258.

(Continued)

*Primary Examiner* — Shanon A. Foley
(74) *Attorney, Agent, or Firm* — Riverside Law LLP

(57) ABSTRACT

The present invention relates to compositions and methods for the treatment and prevention of canine influenza virus (CIV) and CIV-related pathology. The present invention is based in part upon the discovery that one or more mutations in segment 4 of the viral genome produces a single cycle infectious CIV (sciCIV). The sciCIV does not allow for the production of infectious progeny, but is able to induce a CIV-specific immune response.

8 Claims, 7 Drawing Sheets
Specification includes a Sequence Listing.

(56) References Cited

OTHER PUBLICATIONS

Song et al., 2012, "A novel reassortant canine H3N1 influenza virus between pandemic H1N1 and canine H3N2 Influenza viruses in Korea." The Journal of General Virology, 93: 551-554.
Yen et al., 2009, "Pandemic influenza as a current threat." Current topics in microbiology and immunology, 333: 3-24.
Pica et al., 2013, "Toward a universal influenza virus vaccine: prospects and challenges." Annual Review of Medicine, 64: 189-202.
Wong et al., 2013, "Traditional and new influenza vaccines." Clinical Microbiology Reviews, 26: 476-492.
Belshe et al., 2007, "Live attenuated versus inactivated influenza vaccine in infants and young children." The New England Journal of Medicine, 356: 685-696.
Cox et al., 2008, "FluBlok, a recombinant hemagglutinin influenza vaccine." Influenza and other Respiratory Viruses: 2: 211-219.
Osterholm et al., 2012, "Efficacy and effectiveness of influenza vaccines: a systematic review and meta-analysis" The Lancet Infectious Diseases, 12: 36-44.
Pronker et al., 2012, "Development of new generation influenza vaccines: recipes for success?" Vaccine, 30: 7344-7347.
Belongia et al., 2009, "Effectiveness of inactivated influenza vaccines varied substantially with antigenic match from the 2004-2005 season to the 2006-2007 season." Journal of Infectious Diseases, 199: 159-167.
Gorse et al., 1991, "Superiority of live attenuated compared with inactivated influenza A virus vaccines in older, chronically ill adults." Chest, 100: 977-984.
Maassab., 1968, "Plaque formation of influenza virus at 25 degrees C." Nature, 219:645-646.
Cox et al., 1988, "Identification of sequence changes in the cold-adapted, live attenuated influenza vaccine strain, A/Ann Arbor/6/60 (H2N2)." Virology, 167:554-567.
Snyder et al., 1988, "Four viral genes independently contribute to attenuation of live influenza A/Ann Arbor/6/60 (H2N2) cold-adapted reassortant virus vaccines." J Virol, 62:488-495.
Chan et al., 2008, "The cold adapted and temperature sensitive influenza A/Ann Arbor/6/60 virus, the master donor virus for live attenuated influenza vaccines, has multiple defects in replication at the restrictive temperature." Virology, 380:304-311.
Cox et al., 2015, "Development of a mouse-adapted live attenuated influenza virus that permits in vivo analysis of enhancements to the safety of live attenuated influenza virus vaccine." J Virol, 89(6): 3421-3426.
Jin et al., 2004, "Imparting temperature sensitivity and attenuation in ferrets to A/Puerto Rico/8/34 influenza virus by transferring the genetic signature for temperature sensitivity from cold-adapted A/Ann Arbor/6/60." J Virol, 78:995-998.
Zhou et al., 2012, "Engineering temperature sensitive live attenuated influenza vaccines from emerging viruses." Vaccine, 30: 3691-3702.
Martinez-Sobrido et al., 2010, Journal of visualized experiments, 42; doi: 10.3791/2057.
Nogales et al., 2014, "Influenza A virus attenuation by codon deoptimization of the NS gene for vaccine development." J Virol, 88: 10525-10540.
Feng et al., 2015, "Equine and Canine Influenza H3N8 Viruses Show Minimal Biological Differences Despite Phylogenetic Divergence." J Virol, 89: 6860-6873.
Nogales et al., 2015, "Replication-competent influenza A viruses expressing a red fluorescent protein." Virology, 476: 206-216.
Jin et al., 2003, "Multiple amino acid residues confer temperature sensitivity to human influenza virus vaccine strains (FluMist) derived from cold-adapted A/Ann Arbor/6/60." Virology, 306: 18-24.
Nogales et al., 2016, "Rearrangement of Influenza Virus Spliced Segments for the Development of Live-Attenuated Vaccines." J Virol, 90: 6291-6302.
Maassab, 1999, Reviews in medical virology, 9: 237-244.
Murphy et al., 2002, "Principles underlying the development and use of live attenuated cold-adapted influenza A and B virus vaccines." Viral immunology, 15: 295-323.
Kohlmeier et al., 2009, "Immunity to respiratory viruses." Annual review of immunology, 27: 61-82.
Cheng et al., 2013, The Journal of infectious diseases, 208: 594-602.
De Villiers et al., 2009, "Efficacy and safety of a live attenuated influenza vaccine in adults 60 years of age and older." Vaccine, 28: 228-234.
Katsura et al., 2012, "A replication-incompetent virus possessing an uncleavable hemagglutinin as an influenza vaccine." Vaccine, 30: 6027-6033.
Victor et al., 2012, "A replication-incompetent PB2-knockout influenza A virus vaccine vector." J Virol, 86(8): 4123-4128.
Baker et al., 2013, "Protection against lethal influenza with a viral mimic." J Virol, 87: 8591-8605.
Guo et al., 2014, "Induction of CD8 T cell heterologous protection by a single dose of single-cycle infectious influenza virus." J Virol, 88: 12006-12016.
Powell et al., 2012, "Pseudotyped influenza A virus as a vaccine for the induction of heterotypic immunity." J Virol, 86: 13397-13406.
Uraki et al., 2013, "A novel bivalent vaccine based on a PB2-knockout influenza virus protects mice from pandemic H1N1 and highly pathogenic H5N1 virus challenges." J Virol, 87: 7874-7881.
Hayward et al., 2010, "Microevolution of canine influenza virus in shelters and its molecular epidemiology in the United States." J Virol, 84:12636-12645.
Rivailler et al., 2010, "Evolution of canine and equine influenza (H3N8) viruses co-circulating between 2005 and 2008." Virology, 408: 71-79.
Bean et al., 1992, "Evolution of the H3 influenza virus hemagglutinin from human and nonhuman hosts." J Virol, 66:1129-1138.
Both et al., 1983, "Antigenic drift in influenza virus H3 hemagglutinin from 1968 to 1980: multiple evolutionary pathways and sequential amino acid changes at key antigenic sites." J Virol, 48:52.
Bush et al., 1999, "Positive selection on the H3 hemagglutinin gene of human influenza virus A." Molecular biology and evolution, 16: 1457-1465.
De Jong et al., 2007, "Antigenic and genetic evolution of swine influenza A (H3N2) viruses in Europe." J Virol, 81: 4315-4322.
Epperson et al., 2013, Human infections with influenza A(H3N2) variant virus in the United States, 2011-2012. Clinical Infectious diseases, 57 Suppl 1:S4-S11.
Hussain et al., 2010, "Comparison of egg and high yielding MDCK cell-derived live attenuated influenza virus for commercial production of trivalent influenza vaccine: in vitro cell susceptibility and influenza virus replication kinetics in permissive and semi-permissive cells." Vaccine, 28: 3848-3855.
Parrish et al., 2005, "The Origins of New Pandemic Viruses: The Acquisition of New Host Ranges by Canine Parvovirus and Influenza A Viruses" Annual review of microbiology, 59:553-586.
Parrish et al., 2015, "Influenza Virus Reservoirs and Intermediate Hosts: Dogs, Horses, and New Possibilities for Influenza Virus Exposure of Humans" J Virol, 89:2990-2994.
Belshe et al., 2000, "Correlates of Immune Protection Induced by Live, Attenuated, Cold-Adapted, Trivalent, Intranasal Influenza Virus Vaccine" The Journal of infectious diseases, 181:1133-1137.
Centers for Disease Control and Prevention, 2010, "Licensure of a High-Dose Inactivated Influenza Vaccine for Persons Aged ≥65 Years (Fluzone High-Dose) and Guidance for Use—United States, 2010" MMWR, 59(16):485-486.
Rimmelzwaan et al., 2007, "Influenza virus-specific cytotoxic T lymphocytes: a correlate of protection and a basis for vaccine development" Current opinion in biotechnology, 18:529-536.
Smith et al., 2009, "Origins and evolutionary genomics of the 2009 swine-origin H1N1 influenza A epidemic" Nature, 459:1122-1125.
Dundon et al., 2010, "Serologic Evidence of Pandemic (H1N1) 2009 Infection in Dogs, Italy" Emerging infectious diseases, 16:2019-2021.
Hale et al., 2008, "The multifunctional NS1 protein of influenza A viruses" The Journal of general virology, 89:2359-2376.

(56) References Cited

OTHER PUBLICATIONS

Lamb et al., 1980, "Mapping of the two overlapping genes for polypeptides NS1 and NS2 on RNA segment 8 of influenza virus genome" Proceedings of the National Academy of Sciences, 77:1857-1861.

Garcia-Sastre et al., 1998, "Influenza A Virus Lacking the NS1 Gene Replicates in Interferon-Deficient Systems" Virology, 252:324-330.

Steidle et al., 2010, "Glycine 184 in Nonstructural Protein NS1 Determines the Virulence of Influenza A Virus Strain PR8 without Affecting the Host Interferon Response" J Virol, 84:12761-12770.

Geiss et al., 2002, "Cellular transcriptional profiling in influenza A virus-infected lung epithelial cells: The role of the nonstructural NS1 protein in the evasion of the host innate defense and its potential contribution to pandemic influenza" Proceedings of the National Academy of Sciences, 99:10736-10741.

Falcon et al., 2005, "Attenuation and immunogenicity in mice of temperature-sensitive influenza viruses expressing truncated NS1 proteins" The Journal of general virology, 86:2817-2821.

Ferko et al., 2004, "Immunogenicity and Protection Efficacy of Replication-Deficient Influenza A Viruses with Altered NS1 Genes" J Virol, 78:13037-13045.

Quinlivan et al., 2005, "Attenuation of Equine Influenza Viruses through Truncations of the NS1 Protein" J Virol, 79:8431-8439.

Richt et al., 2009, "Attenuated Influenza Virus Vaccines with Modified NS1 Proteins" Current topics in microbiology and Immunology, 333:177-195.

Steel et al., 2009, "Live Attenuated Influenza Viruses Containing NS1 Truncations as Vaccine Candidates against H5N1 Highly Pathogenic Avian Influenza" J Virol 83:1742-1753.

Vincent et al., 2007, "Efficacy of intranasal administration of a truncated NS1 modified live influenza virus vaccine in swine" Vaccine 25:7999-8009.

Richt et al., 2006, "Vaccination of Pigs against Swine Influenza Viruses by Using an NS1-Truncated Modified Live-Virus Vaccine" J Virol 80:11009-11018.

Solorzano et al., 2005, "Mutations in the NS1 Protein of Swine Influenza Virus Impair Anti-Interferon Activity and Confer Attenuation in Pigs" J Virol, 79:7535-7543.

Choi et al., 2015, "Development of a dual-protective live attenuated vaccine against H5N1 and H9N2 avian influenza viruses by modifying the NS1 gene" Archives of virology, 160:1729-1740.

Wang et al., 2008, "Characterization of influenza virus variants with different sizes of the non-structural (NS) genes and their potential as a live influenza vaccine in poultry" Vaccine, 26:3580-3586.

Baskin et al., 2007, "Functional Genomic and Serological Analysis of the Protective Immune Response Resulting from Vaccination of Macaques with an NS1-Truncated Influenza Virus" J Virol, 81:11817-11827.

Pica et al., 2012, "NS1-Truncated Live Attenuated Virus Vaccine Provides Robust Protection to Aged Mice from Viral Challenge" J Virol, 86:10293-10301.

Hai et al., 2008, "Influenza B Virus NS1-Truncated Mutants: Live-Attenuated Vaccine Approach" J Virol, 82:10580-10590.

Talon et al., 2000, "Influenza A and B viruses expressing altered NS1 proteins: A vaccine approach" Proceedings of the National Academy of Sciences, 97:4309-4314.

Martinez-Sobrido et al., 2009, "Identification of Amino Acid Residues Critical for the Anti-Interferon Activity of the Nucleoprotein of the Prototypic Arenavirus Lymphocytic Choriomeningitis Virus" J Virol, 83:11330-11340.

Martinez-Sobrido et al., 2006, "Inhibition of the type I interferon response by the nucleoprotein of the prototypic arenavirus lymphocytic choriomeningitis virus" J Virol, 80:9192-9199.

Park et al., 2003, "Newcastle Disease Virus (NDV)-Based Assay Demonstrates Interferon-Antagonist Activity for the NDV V Protein and the Nipah Virus V, W, and C Proteins" J Virol, 77:1501-1511.

Deshpande et al., 2009, "Evaluation of the Efficacy of a Canine Influenza Virus (H3N8) Vaccine in Dogs Following Experimental Challenge" Veterinary therapeutics: research in applied veterinary medicine, 10:103-112.

Newbury et al., 2016, "Prolonged intermittent virus shedding during an outbreak of canine influenza A H3N2 virus infection in dogs in three Chicago area shelters: 16 cases (Mar. to May 2015)" Journal of the American Veterinary Medical Association, 248:1022-1026.

Ramirez-Martinez et al., 2013, "Evidence of transmission and risk factors for influenza A virus in household dogs and their owners" Influenza and other respiratory viruses, 7:1292-1296.

Randall et al., 2008, "Interferons and viruses: an interplay between induction, signalling, antiviral responses and virus countermeasures" The Journal of general virology, 89:1-47.

Solorzano et al., 2010, "Alternative Live-Attenuated Influenza Vaccines Based on Modifications in the Polymerase Genes Protect against Epidemic and Pandemic Flu." Journal of Virology, 84(9): 4587-4596.

Song et al., 2007, "A New Generation of Modified Live-Attenuated Avian Influenza Viruses Using a Two-Strategy Combination as Potential Vaccine Candidates." Journal of Virology, 81(17): 9238-9248.

Subbarao et al., 1995, "Sequential addition of temperature-sensitive missense mutations into the PB2 gene of Influenza A transfectant viruses can effect an increase in temperature sensitivity and attenuation and permits the rational design of a genetically engineered live influenza A virus vaccine." Journal of Virology, 69(10): 5969-5977.

Hickman et al., 2008, "An avian live attenuated master backbone for potential use in epidemic and pandemic influenza vaccines." Journal of General Virology, 89(11): 2682-2690.

Mariana Baz et al., 2014, "A live attenuated H3N8 influenza vaccine is highly immunogenic and efficacious in mice and ferrets." Journal of Virology, 89(3): 1652-1659.

Kappes et al., 2011, "Vaccination with NS-1 truncated H3N2 swine influenza virus rimes T cells and confers cross-protection against an H1N1 heterosubtypic challenge in pigs." Vaccine, 30(2): 280-288.

Voorhees et al., "Spread of Canine Influenza A9H3N2) Virus, United States," Emerging Infectious Diseases, 23 (12):1950-1957, 2017.

Chao, "A Single Amino Acid Deletion at the Amino Terminus of Influenza Virus Hemagglutinin Causes Malfolding and Blocks Exocytosis of the Molecule in Mammalian Cells," The Journal of Biological Chemistry, 267(4)2142-2148, 1992.

Murphy et al., "An influenza A live attenuated reassortant virus possessing three temperature-sensitive mutations in the PB2 polymerase gene rapidly loses temperature sensitivity following replication in hamsters," Vaccine, 15 (12/13):1372-1378, 1997.

Hanson et al., "Canine Influenza," Clinicians Brief, University of Georgia, 97-103, 2016.

Suzuki et al., "Amino Acid Substitutions of PB1 of Avian Influenza Viruses Influence Pathogenicity and Transmissibility in Chickens," Journal of Virology, 88(19):11130-11139, 2014.

\* cited by examiner

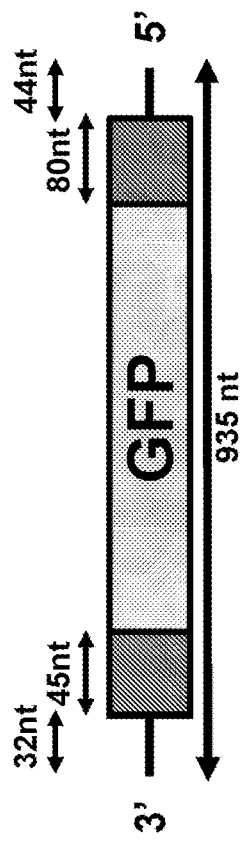
Figure 2A
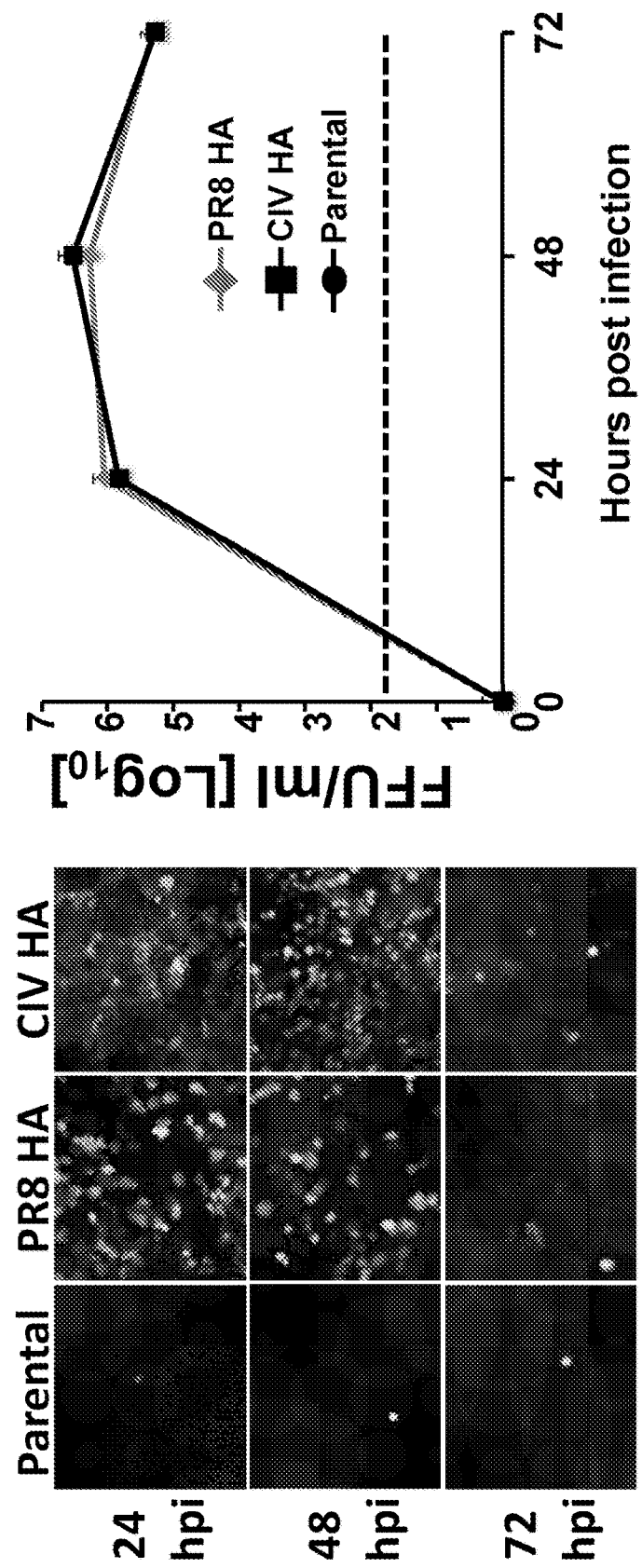
Figure 2B
Figure 2C

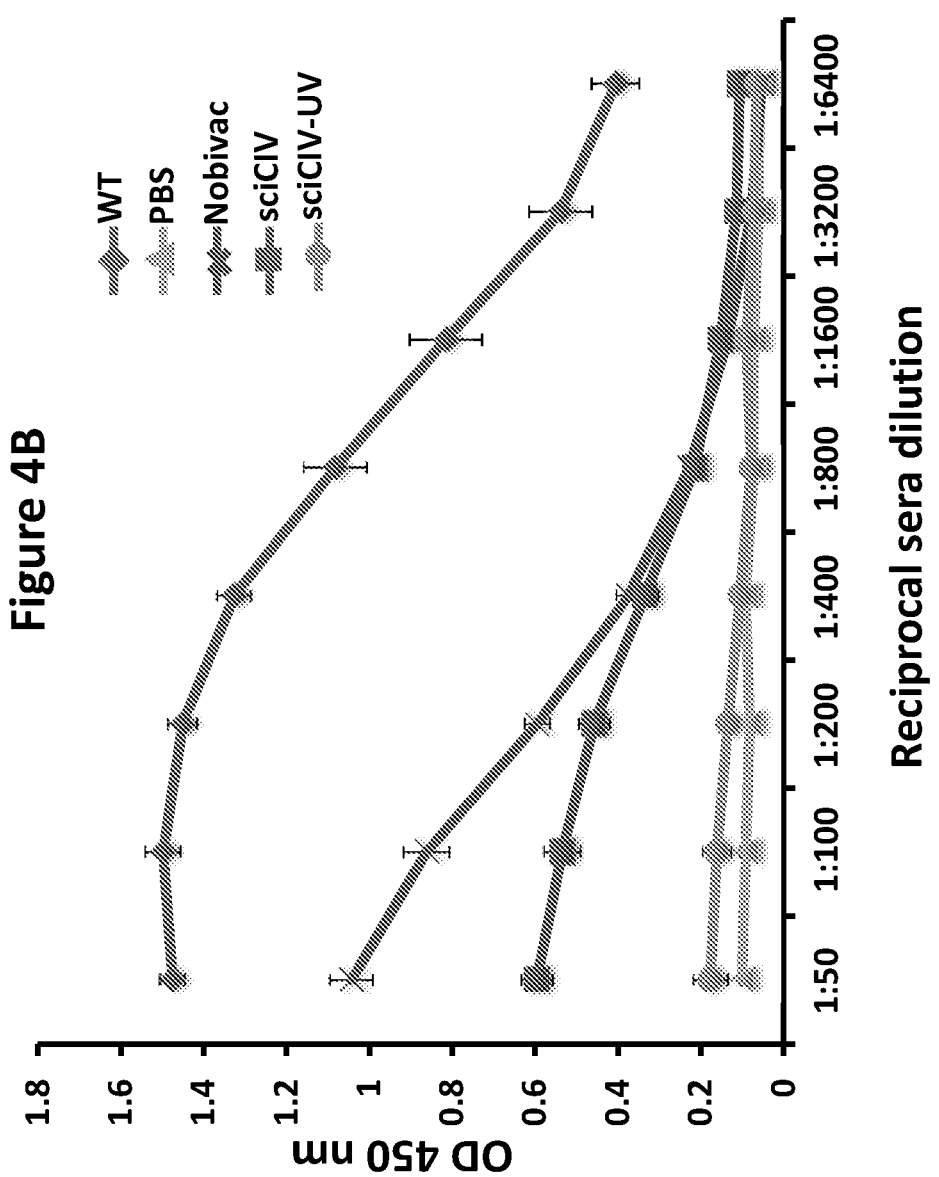
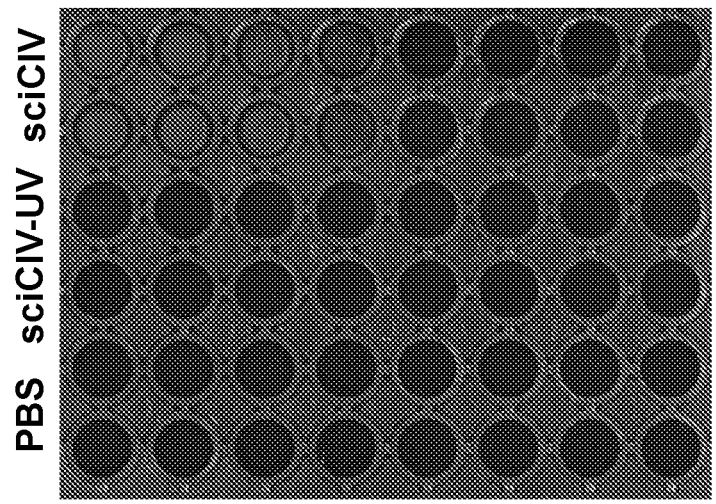

SEQUENCE LISTING

```
<160> NUMBER OF SEQ ID NOS: 18

<210> SEQ ID NO 1
<211> LENGTH: 2341
<212> TYPE: DNA
<213> ORGANISM: Influenza A virus (H3N8)

<400> SEQUENCE: 1
agcgaaagca ggtcaaatat attcaatatg gagagaataa aagaactgag agatctgatg      60
ttacaatccc gcacccgcga gatactaaca aaaactactg tagaccacat ggccataatc     120
aagaaataca catcaggaag acaagagaag aaccctgcac ttaggatgaa atggatgatg     180
gcaatgaaat acccaatcac agcagataag aggataatgg agatgattcc tgagagaaat     240
gaacagggac aaaccctttg gagcaaaacg aacgatgctg gctcagaccg cgtaatggta     300
tcacctctgg cagtaacatg gtggaatagg aatggaccaa caacgaacac aattcattat     360
ccaaaagtct acaaaactta ttttgaaaag gttgaaagat tgaaacacgg aacctttggc     420
cccgttcatt ttaggaatca agtcaaaata agacgaagag ttgatgtaaa ccctggtcac     480
gcggacctca gtgctaaaga agcacaagat gtgatcatgg aagttgtttt cccaaatgag     540
gtgggagccc gaattctaac atcggaatca caactaacaa taaccaagga gaaaaaggaa     600
gaacttcagg actgcaaaat tgctcccttg atggtagcat acatgctaga aagagagttg     660
gtccgaaaaa caaggttcct cccagtagta ggcggaacaa gcagtatata cattgaagtg     720
ttgcatctga ctcagggaac atgctgggag caaatgtaca ccccaggagg agaagttaga     780
aacgatgata ttgatcaaag tttaattatt gcagcccgga acatagtgag aagagcgaca     840
gtatcagcag atccactagc atccctactg gaaatgtgcc acagtacaca aattggtgga     900
acaaggatga tagacatcct taagcagaac ccaacagagg aacaagctgt ggatatatgc     960
```

```
aaagcagcaa tgggattgag aattagctca tcattcagct ttggtggatt caccttcaaa    1020
aggacaagtg atcatcagt caagagagaa gaagaaatgc ttacgggcaa ccttcaaaca    1080
ttgaaaataa gagtgcatga gggctatgaa gaattcacaa tggtcggaag aagagcaaca    1140
gccattatca gaaaggcaac cagaagattg attcaactga tagtaagtgg aaaagatgaa    1200
caatcaattg ctgaagcaat aattgtagcc atggtgtttt cgcaagaaga ttgcatgata    1260
aaagcagttc gaggcgattt gaactttgtt aatagagcaa atcagcgttt aaaccccatg    1320
catcaactct tgaggcattt ccaaaaagat gcaaagtgc ttttccaaaa ttggggaatt    1380
gaacccatcg acaatgtaat gggaatgatt ggaatactgc ctgacatgac cccaagcact    1440
gaaatgtcat tgagaggagt gagagtcagc aaaatgggag tggatgagta ctccagcact    1500
gagagagtgg tggtgagcat tgaccgtttt ttaagagttc gggatcaaag gggaaacata    1560
ctactgtccc ctgaagaagt cagtgaaaca caaggaacgg aaaagctgac aataatttat    1620
tcgtcatcaa tgatgtggga gattaatggt cccgaatcag tgttggtcaa tacttatcaa    1680
tggatcatca gaaactggga aaatgtaaaa attcagtggt cacaggaccc cacaatgtta    1740
tacaataaga tagaatttga gccattccaa tccctggtcc ctagggccac cagaagccaa    1800
tacagcggtt ttgtaagaac cctgtttcag caaatgcgag atgtacttgg aacatttgat    1860
actgctcaaa taataaaact cctccctttt gccgctgctc ctccggaaca gagtaggatg    1920
cagttctctt ctttgactgt taatgtaaga ggttcgggaa tgaggatact tgtaagaggc    1980
aattccccag tgttcaacta caataaagcc actaaaaggc tcacagtcct cggaaaagat    2040
gcgggtgcgc ttactgagga cccagatgaa ggtacggctg gagtagaatc cgctgttcta    2100
agagggtttc tcatcttagg taaagaaaac aagagatatg gcccagcact aagcatcaat    2160
gaacttagca aacttgcaaa aggggagaaa gccaatgtac taattgggca aggggacata    2220
gtgttggtaa tgaaacggaa acgtgactct agcatactta ctgacagcca gacagcgacc    2280
aaaaggattc ggatggccat caattagtgt taaattgttt aaaaacgacc ttgtttctac    2340
t                                                                  2341
```

<210> SEQ ID NO 2
<211> LENGTH: 759
<212> TYPE: PRT
<213> ORGANISM: Influenza A virus (H3N8)

<400> SEQUENCE: 2

```
Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Met
        50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
            100                 105                 110

Lys Val Tyr Lys Thr Tyr Phe Glu Lys Val Glu Arg Leu Lys His Gly
        115                 120                 125
```

```
Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Val Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Thr Arg Met Ile Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Ile Arg Lys Ala Thr Arg Arg Leu Ile Gln Leu
    370                 375                 380

Ile Val Ser Gly Lys Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540
```

-continued

Val Leu Val Asn Thr Tyr Gln Trp Ile Ile Arg Asn Trp Glu Asn Val
545                 550                 555                 560

Lys Ile Gln Trp Ser Gln Asp Pro Thr Met Leu Tyr Asn Lys Ile Glu
            565                 570                 575

Phe Glu Pro Phe Gln Ser Leu Val Pro Arg Ala Thr Arg Ser Gln Tyr
        580                 585                 590

Ser Gly Phe Val Arg Thr Leu Phe Gln Gln Met Arg Asp Val Leu Gly
    595                 600                 605

Thr Phe Asp Thr Ala Gln Ile Ile Lys Leu Leu Pro Phe Ala Ala Ala
610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
                660                 665                 670

Gly Ala Leu Thr Glu Asp Pro Asp Glu Gly Thr Ala Gly Val Glu Ser
            675                 680                 685

Ala Val Leu Arg Gly Phe Leu Ile Leu Gly Lys Glu Asn Lys Arg Tyr
690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Ile Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 3
<211> LENGTH: 2341
<212> TYPE: DNA
<213> ORGANISM: Influenza A virus (H3N8)

<400> SEQUENCE: 3
agcgaaagca ggcaaaccat ttgaatggat gtcaacccga ctctactttt cttaaaggtg      60
ccagcgcaaa atgctataag cacaacattc ccttatactg gagatcctcc ctacagtcat     120
ggaacaggga caggatacac catggatact gtcaacagaa cgcaccaata ttcagaaaaa     180
gggaaatgga taacaaacac tgagattgga gcaccacaac ttaatccaat cgatggacca     240
cttcctgaag acaatgaacc aagtgggtac gcccaaacag attgtgtatt ggaagcaatg     300
gctttccttg aagaatccca tcccggaatc tttgaaaatt cgtgtcttga acaatggag      360 gtgattcagc agacaagagt ggacaaacta acacaaggcc gacaaactta tgattggacc     420
ttgaatagga tcaacctgc cgcaacagca cttgctaata cgattgaagt attcagatca     480
aatggtctga cttccaatga atcggggaga ttgatagact cctcaaaga tgtcatggag      540 tccatgaaca aggaagaaat ggaataaca acacacttcc aacggaagag aagagtaaga     600
gacaacatga caaagagaat gataacacag agaaccatag ggaagaaaaa acaacgatta     660
aacagaaaga gctatctgat cagaacatta accctaaaca caatgaccaa ggacgctgag     720
agagggaaat tgaaacgacg agcaatcgct accccaggga tgcagataag aggatttgta     780
tattttgttg aaacactagc tcgaagaata tgtgaaaagc ttgaacaatc aggattgcca     840
gttggcggta atgagaaaaa agccaaactg gctaatgtcg tcagaaaaat gatgactaat     900

```
tcccaagaca ctgaactctc cttcaccatc actggggaca ataccaaatg gaatgaaaat    960
cagaacccac gcatattcct ggcaatgatc acatacataa ctagaaatca gccagaatgg   1020
ttcagaaatg ttctaaacat tgcaccgatt atgttctcaa ataaaatggc aagactgggg   1080
aaaggatata tgtttgaaag caaaagtatg aaattgagaa ctcaaatacc agcagaaatg   1140
ctagcgagca ttgacctaaa atatttcaat gattcaacaa aaagaaaat tgaaagata    1200
cgaccactct tggttaacgg gactgcttca ctgagtcctg gcatgatgat gggaatgttc   1260
aacatgttga gcactgtgct gggtgtatcc atattaaacc tgggccagag gaaatataca   1320
aaaccacat actggtggga tggtctgcaa tcatcagatg actttgcttt gatagtgaat   1380
gcgcctaatc atgaaggaat acaagctgga gtagacagat tctatagaac ttgcaaactg   1440
gtcgggatca acatgagcaa aaagaagtcc tacataaata gaactggaac attcgaattc   1500
acaagctttt tctaccggta tggttttgta gccaatttca gcatggaact acccagtttt   1560
ggggtttccg gaataaatga atctgcagac atgagcattg gagtgacaat catcaaaaac   1620
aacatgataa ataatgatct cggtcctgcc acggcacaaa tggcactcca actcttcatt   1680
aaggattatc ggtacacata ccggtgccat agaggtgata cccagataca aaccagaaga   1740
tcttttgagt tgaagaaact ttgggaacag actcaatcaa agactggtct actgatatca   1800
gatgggggtc caaacctata taacatcaga aacctacaca tcccggaagt ctgtttaaag   1860
tgggagctaa tggatgaaga ttataagggg aggctatgca atccattgaa tccttcgtt   1920
agtcacaaag aaattgaatc agtcaacagt gcagtagtaa tgcctgcgca tggccctgcc   1980
aaaagcatgg agtatgatgc tgttgcaaca acacattctt ggatcccaa gaggaaccgg   2040
tccatattga acacaagcca aggggaata ctcgaagatg agcatatgta tcagaaatgc   2100
tgcaacctgt ttgaaaaatt cttcccaagc agctcataca gaagaccagt cggaatttct   2160
agtatggttg aggccatggt atccagggcc cgcattgatg cacgaattga cttcgaatct   2220
ggacggataa agaaggatga gttcgctgag atcatgaaga tctgttccac cattgaagag   2280
ctcaaacggc aaaaatagtg aatttagctt gatcttcatg aaaaaatgcc ttgtttctac   2340
t                                                                 2341
```

<210> SEQ ID NO 4
<211> LENGTH: 757
<212> TYPE: PRT
<213> ORGANISM: Influenza A virus (H3N8)

<400> SEQUENCE: 4

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Ile Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110
```

-continued

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ser Asn Glu Ser
145                 150                 155                 160

Gly Arg Leu Ile Asp Phe Leu Lys Asp Val Met Glu Ser Met Asn Lys
                165                 170                 175

Glu Glu Met Glu Ile Thr Thr His Phe Gln Arg Lys Arg Val Arg
            180                 185                 190

Asp Asn Met Thr Lys Arg Met Ile Thr Gln Arg Thr Ile Gly Lys Lys
            195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Asn Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asn Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
    435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

-continued

```
Ile Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Gln Ser Lys Thr Gly Leu Leu Ile Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu His Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Lys Arg Gln Lys
        755
```

<210> SEQ ID NO 5
<211> LENGTH: 2233
<212> TYPE: DNA
<213> ORGANISM: Influenza A virus (H3N8)

<400> SEQUENCE: 5

```
agcgaaagca ggtactgatc caaaatggaa gactttgtgc gacagtgctt caatccaatg      60
atcgtcgagc ttgcggaaaa ggcaatgaaa gaatatggag agaacccgaa aatcgaaaca     120
aacaaatttg cagcaatatg cactcacttg gaagtctgct tcatgtactc ggatttccac     180
tttataaatg aactgggtga gtcagtggtc atagagtctg gtgacccaaa tgctcttttg     240
aaacacagat ttgaaatcat tgaggggaga gatcgaacaa tggcatggac agtagtaaac     300
agcatctgca acaccacaag agctgaaaaa cctaaatttc ttccagattt atacgactat     360
aaggagaaca gatttgttga aattggtgtg acaaggagag aagttcacat atactacctg     420
gagaaggcca acaaaataaa gtctgagaaa acacatatcc acatcttctc atttacagga     480
gaggaaatgg ctacaaaagc ggactatact cttgatgaag agagtagagc caggatcaag     540
accagactat tcactataag acaagaaatg gccagtagag gcctctggga ttcctttcgt     600
cagtccgaga gaggcgaaga gacaattgaa gaaagatttg aaatcacagg gacgatgcgc     660
aagcttgcca attacagtct cccaccgaac ttctccagcc ttgaaaattt tagagtttat     720
gtagatggat tcgaaccgaa cggctgcatt gagagtaagc tttctcaaat gtccaaagaa     780
```

-continued

```
gtaaatgcca aaatcgaacc attttcaaag acaacacccc gaccactcaa aatgcctggt      840
ggtccaccct gccatcagcg atccaaattc ttgctaatgg atgctctgaa attgagcatt      900
gaagacccaa gtcacgaggg agaagggata ccactatatg atgcaatcaa atgcatgaaa      960
actttctttg gatggaaaga acccagtatt gttaaaccac ataaaaaggg tataaacccg     1020
aactatctcc aaacttggaa gcaagtatta gaagaaatac aagacattga gaacgaagaa     1080
aagaccccca aaccaagaa tatgaaaaaa acaagccaat aaaatgggc actaggtgaa       1140
aatatggcac cagagaaagt ggattttgag gattgtaaag acatcaatga tttaaaacaa     1200
tatgacagtg atgagccaga agcaaggtct cttgcaagtt ggattcaaag tgagttcaac     1260
aaggcttgtg agctgacaga ttcaagctgg atagagctcg atgaaattgg ggaggatgtc     1320
gccccaatag aatacattgc gagcatgagg agagactatt ttactgctga gatttcccat     1380
tgtagagcaa cagaatatat aatgaaagga gtatacatca acactgctct actcaatgca     1440
tcctgtgctg cgatggatga atttcaattg attccgatga taagtaaatg caggaccaaa     1500
gaagggagaa ggaaaacaaa tttatatgga ttcataataa agggaaggtc ccatttaaga     1560
aatgatactg acgtggtgaa ctttgtaagt atggaatttt ctctcactga tccaagattt     1620
gagccacaca aatgggaaaa atactgcgtt ctagaaattg agacatgct tctaagaact      1680
gctgtaggtc aagtgtcaag acccatgttt ttatatgtaa ggacaaatgg aacctctaaa     1740
attaaaatga atgggggaat ggaaatgagg cgctgcctcc ttcagtctct acaacagatt     1800
gaaagcatga tcgaagctga gtcctcagtc aaagaaaagg acatgaccaa gaatttttt    1860
gagaacaaat cagagacatg gcctatagga gagtccccca aaggagtgga agaaggctca    1920
atcgggaagg tttgcaggac cttattagca aaatctgtgt ttaacagttt atatgcatct    1980
ccacaactgg aaggattttc agctgaatct aggaaattac ttctcattgt tcaggctctt    2040
agagatgacc tggaacctgg aaccttttgat attgggggt tatatgaatc aattgaggag    2100
tgcctgatta atgatccctg ggttttgctt aatgcatctt ggttcaactc cttcctcaca    2160
catgcactga agtagttgtg gcaatgctac tatttgctat ccatactgtc caaaaaagta    2220
ccttgtttct act                                                        2233
```

<210> SEQ ID NO 6
<211> LENGTH: 716
<212> TYPE: PRT
<213> ORGANISM: Influenza A virus (H3N8)

<400> SEQUENCE: 6

```
Met Glu Asp Phe Val Arg Gln Cys Phe Asn Pro Met Ile Val Glu Leu
1               5                   10                  15
Ala Glu Lys Ala Met Lys Glu Tyr Gly Glu Asn Pro Lys Ile Glu Thr
            20                  25                  30
Asn Lys Phe Ala Ala Ile Cys Thr His Leu Glu Val Cys Phe Met Tyr
        35                  40                  45
Ser Asp Phe His Phe Ile Asn Glu Leu Gly Glu Ser Val Val Ile Glu
    50                  55                  60
Ser Gly Asp Pro Asn Ala Leu Leu Lys His Arg Phe Glu Ile Ile Glu
65                  70                  75                  80
Gly Arg Asp Arg Thr Met Ala Trp Thr Val Val Asn Ser Ile Cys Asn
                85                  90                  95
Thr Thr Arg Ala Glu Lys Pro Lys Phe Leu Pro Asp Leu Tyr Asp Tyr
            100                 105                 110
```

```
Lys Glu Asn Arg Phe Val Glu Ile Gly Val Thr Arg Glu Val His
            115                 120                 125
Ile Tyr Tyr Leu Glu Lys Ala Asn Lys Ile Lys Ser Glu Lys Thr His
130                 135                 140
Ile His Ile Phe Ser Phe Thr Gly Glu Glu Met Ala Thr Lys Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Ser Arg Gly Leu Trp Asp Ser Phe Arg
            180                 185                 190
Gln Ser Glu Arg Gly Glu Glu Thr Ile Glu Glu Arg Phe Glu Ile Thr
        195                 200                 205
Gly Thr Met Arg Lys Leu Ala Asn Tyr Ser Leu Pro Pro Asn Phe Ser
    210                 215                 220
Ser Leu Glu Asn Phe Arg Val Tyr Val Asp Gly Phe Glu Pro Asn Gly
225                 230                 235                 240
Cys Ile Glu Ser Lys Leu Ser Gln Met Ser Lys Glu Val Asn Ala Lys
                245                 250                 255
Ile Glu Pro Phe Ser Lys Thr Thr Pro Arg Pro Leu Lys Met Pro Gly
            260                 265                 270
Gly Pro Pro Cys His Gln Arg Ser Lys Phe Leu Leu Met Asp Ala Leu
        275                 280                 285
Lys Leu Ser Ile Glu Asp Pro Ser His Glu Gly Glu Gly Ile Pro Leu
    290                 295                 300
Tyr Asp Ala Ile Lys Cys Met Lys Thr Phe Phe Gly Trp Lys Glu Pro
305                 310                 315                 320
Ser Ile Val Lys Pro His Lys Lys Gly Ile Asn Pro Asn Tyr Leu Gln
                325                 330                 335
Thr Trp Lys Gln Val Leu Glu Glu Ile Gln Asp Ile Glu Asn Glu Glu
            340                 345                 350
Lys Thr Pro Lys Thr Lys Asn Met Lys Lys Thr Ser Gln Leu Lys Trp
        355                 360                 365
Ala Leu Gly Glu Asn Met Ala Pro Glu Lys Val Asp Phe Glu Asp Cys
    370                 375                 380
Lys Asp Ile Asn Asp Leu Lys Gln Tyr Asp Ser Asp Glu Pro Glu Ala
385                 390                 395                 400
Arg Ser Leu Ala Ser Trp Ile Gln Ser Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu Tyr Ile Ala Ser Met Arg Arg Asp Tyr Phe Thr Ala
        435                 440                 445
Glu Ile Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Glu Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Phe Glu Pro His Lys Trp Glu Lys Tyr Cys Val Leu Glu
```

```
                530            535            540
Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
                595                 600                 605

Lys Glu Phe Phe Glu Asn Lys Ser Glu Thr Trp Pro Ile Gly Glu Ser
                610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
                660                 665                 670

Arg Asp Asp Leu Glu Pro Gly Thr Phe Asp Ile Gly Gly Leu Tyr Glu
                675                 680                 685

Ser Ile Glu Glu Cys Leu Ile Asn Asp Pro Trp Val Leu Leu Asn Ala
                690                 695                 700

Ser Trp Phe Asn Ser Phe Leu Thr His Ala Leu Lys
705                 710                 715

<210> SEQ ID NO 7
<211> LENGTH: 1762
<212> TYPE: DNA
<213> ORGANISM: Influenza A virus (H3N8)

<400> SEQUENCE: 7
agcaaaagca gggatatttt ctttcaatca tgaaaacaac cattatttta atactactga    60
cccattgggc ctacagtcaa aacccaatca gtggcaataa cacagccaca ctgtgtctgg   120
gacaccatgc agtagcaaat ggaacattgg taaaaacaat gagtgatgat caaattgagg   180
tgacaaatgc tacagaatta gttcagagca tttcaatggg gaaaatatgc aacaaatcat   240
atagagttct agatggaaga aattgcacat taatagatgc aatgctagga gaccccagt   300 gtgacgcctt tcagtatgag agttgggacc tctttataga agaagcaac gctttcagca   360 attgctaccc atatgacatc cctgactatg catcgctccg atccattgta gcatcctcag   420
gaacagtgga attcacagca gagggattca catggacagg tgtcactcaa aacggaagaa   480
gtggagcctg caaaagggga tcagccgata gtttctttag ccgactgaat tggctaacaa   540
aatctggaag ctcttacccc acattgaatg tgacaatgcc taacaataaa aatttcgaca   600
agctatacat ctgggggatt catcacccga gctcgaatca agagcagaca aaattgtaca   660
tccaagaatc aggacgagta acagtctcaa caaaagaag tcaacaaaca ataatccctc   720
acatcggatc tagaccgttg atcagaggtc aatcaggcag ataagcata tactggacca   780 ttgtaaaacc tggagatatc ctaatgataa acagtaatgg caacttagtt gcaccgcggg   840
gatatttcaa attgaaccca ggaaaaagct ctgtaatgag atccgatgta cccatagaca   900
tttgtgtgtc tgaatgtatt acaccaaatg gaagcatctc caacgacaag ccattccaaa   960
atgtgaacaa agttacatat ggaaaatgcc ccaagtatat caggcaaaac actttaaagt  1020
tggccactgg gatgaggaat gtgccagaaa agcaaaccag aggaatcttt ggggcgatag  1080
```

-continued

```
cgggattcat cgaaaacggc tgggaaggaa tggttgatgg gtggtatggg ttccgatatc   1140
aaaactctga aggaacaggg caagctgcag atctaaagag cactcaagca gccatcgacc   1200
agattaatgg aaagttaaac agggtgattg aaagaaccaa tgagaaattc catcaaatag   1260
agaaggaatt ctcagaagta gaaggaagaa ttcaggactt ggagaaatat gtagaagaca   1320
ccaaaataga cctatggtcc tacaatgcag aactgctggt ggctctagaa aatcaacata   1380
caattgactt aacagatgca gaaatgaata aattatttga gaagactaga cgccagttaa   1440
gagaaaatgc agaagacatg ggagatggat gtttcaagat ttaccacaag tgtgataatg   1500
catgcattga gtcaataaga actggaacat atgaccatta catatacaaa gatgaagcat   1560
taaacaaccg atttcagatc aaaggtgtag aattgaaatc aggctacaaa gattggatac   1620
tgtggatttc attcgccata tcatgcttct taatttgcgt tgttctattg ggtttcatta   1680
tgtgggcttg ccaaaaaggc aacatcagat gcaacatttg catttgagta aactgatagt   1740
taaaaacacc cttgtttcta ct                                            1762

<210> SEQ ID NO 8
<211> LENGTH: 565
<212> TYPE: PRT
<213> ORGANISM: Influenza A virus (H3N8)

<400> SEQUENCE: 8

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Val Leu Asp Gly Arg Asn Cys Thr
65                  70                  75                  80

Leu Ile Asp Ala Met Leu Gly Asp Pro Gln Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro His Ile Gly Ser Arg Pro Leu Ile Arg Gly
225                 230                 235                 240

Gln Ser Gly Arg Ile Ser Ile Tyr Trp Thr Ile Val Lys Pro Gly Asp
                245                 250                 255
```

```
Ile Leu Met Ile Asn Ser Asn Gly Asn Leu Val Ala Pro Arg Gly Tyr
            260                 265                 270

Phe Lys Leu Asn Pro Gly Lys Ser Val Met Arg Ser Asp Val Pro
        275                 280                 285

Ile Asp Ile Cys Val Ser Glu Cys Ile Thr Pro Asn Gly Ser Ile Ser
290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
                340                 345                 350

Phe Ile Glu Asn Gly Trp Glu Gly Met Val Asp Gly Trp Tyr Gly Phe
            355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Lys Glu Phe Ser Glu
                405                 410                 415

Val Glu Gly Arg Ile Gln Asp Leu Glu Lys Tyr Val Glu Asp Thr Lys
                420                 425                 430

Ile Asp Leu Trp Ser Tyr Asn Ala Glu Leu Leu Val Ala Leu Glu Asn
            435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Asp Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Lys Asp Glu Ala Leu Asn
                500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 9
<211> LENGTH: 1565
<212> TYPE: DNA
<213> ORGANISM: Influenza A virus (H3N8)

<400> SEQUENCE: 9
agcaaaagca gggtagataa tcactcactg agtgacatca aagtcatggc gtctcaaggc       60
accaaacgat cctatgaaca gatggaaact gatggggaac gccagaatgc aactgaaatc      120
agaacatctg tcggaaggat ggtgggagga atcggacggt tttatgtcca gatgtgtact      180
gagcttaaac taaacgacta tgaagggcgg ctgattcaga acagcataac aatagaaagg      240
atggtacttt cggcattcga cgaaagaaga aacaagtatc tcgaggagca tcccagtgct      300
```

-continued

```
gggaaagacc ctaagaaaac ggggggcccg atatacagaa gaaaagatgg gaaatggatg    360
agggaactca tcctccatga taaagaagaa atcatgagaa tctggcgtca ggccaacaat    420
ggtgaagacg ctactgctgg tcttactcac atgatgatct ggcactccaa tctcaacgac    480
accacatacc aaagaacaag ggctcttgtt cggactggga tggatcccag aatgtgctct    540
ttgatgcaag gctcaaccct cccacggaga tctggagccg ctggtgctgc agtaaaaggt    600
gttggaacaa tggtaatgga actcatcaga atgatcaagc gcggaataaa tgatcggaat    660
ttctggagag gtgaaaatgg tcgaagaacc agaattgctt atgaaagaat gtgcaatatc    720
ctcaaaggga aatttcagac agcagcacaa cgggctatga tggaccaggt gagggaaggc    780
cgcaaccctg gaaacgctga aattgaggat ctcattttct tggcacgatc agcacttatt    840
ttgagaggat cagtagccca taaatcatgc ctacctgcct gtgtttatgg ccttgcagta    900
accagtgggt atgactttga gaaggaagga tactctctgg ttggaattga tcctttcaaa    960
ctactccaga acagtcaaat tttcagtcta atcagaccaa aagaaaaccc agcacacaaa   1020
agccaattgg tgtggatggc atgccattct gcagcatttg aggatctgag agttttaaat   1080
ttcattagag gaaccaaagt aatcccaaga ggacagttaa caaccagagg agttcaaatt   1140
gcttcaaatg aaaacatgga gacaataaat tctagcacac ttgaactgag aagcaaatat   1200
tgggcaataa gaaccagaag cggaggaaac accagtcaac agagagcatc tgcaggacag   1260
ataagtgtgc aacctacttt ctcagtacag agaaatcttc cctttgagag agcaaccatt   1320
atggctgcat tcactggtaa cactgaaggg aggacttccg acatgagaac ggaaatcata   1380
aggatgatgg aaaatgccaa atcagaagat gtgtctttcc aggggcgggg agtcttcgag   1440
ctctcggacg aaaaggcaac gaacccgatc gtgccttcct ttgacatgag caatgaaggg   1500
tcttatttct tcggagacaa tgctgaggag tttgacaatt aaagaaaaat acccttgttt   1560
ctact                                                                1565

<210> SEQ ID NO 10
<211> LENGTH: 498
<212> TYPE: PRT
<213> ORGANISM: Influenza A virus (H3N8)

<400> SEQUENCE: 10

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Thr Ser Val Gly Arg Met
            20                  25                  30

Val Gly Gly Ile Gly Arg Phe Tyr Val Gln Met Cys Thr Glu Leu Lys
        35                  40                  45

Leu Asn Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140
```

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
            165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
            210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Thr Ser Gly
            275                 280                 285

Tyr Asp Phe Glu Lys Glu Gly Tyr Ser Leu Val Gly Ile Asp Pro Phe
290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
            340                 345                 350

Ile Pro Arg Gly Gln Leu Thr Thr Arg Gly Val Gln Ile Ala Ser Asn
            355                 360                 365

Glu Asn Met Glu Thr Ile Asn Ser Ser Thr Leu Glu Leu Arg Ser Lys
            370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
            435                 440                 445

Glu Asn Ala Lys Ser Glu Asp Val Ser Phe Gln Gly Arg Gly Val Phe
450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Phe
                485                 490                 495

Asp Asn

<210> SEQ ID NO 11
<211> LENGTH: 1461
<212> TYPE: DNA
<213> ORGANISM: Influenza A virus (H3N8)

<400> SEQUENCE: 11
agcaaaagca ggagtttaaa atgaatccaa atcaaaagat aatagcaatt ggatctgcat    60
cattggggat attaatcatt aatgtcattc t

```
tggtcctcaa taacaataga acagatctaa actgcaaagg gacgatcata agagagtaca    180
atgaaacagt aagagtagaa aaacttactc aatggtataa tatcagtaca attaagtaca    240
tagagagacc ttcaaatgaa tattacatga caacactga accactttgt gaggcccaag    300
gctttgcacc attttccaaa gataatggaa tacgaattgg gtcgagaggc catgttttttg   360
tgataagaga accttttgta tcatgttcac cctcagaatg tagaaccttt ttcctcacac    420
agggctcatt actcaatgac aaacattcta acggcacaat aaaggatcga agtccgtata    480
ggactctgat gagtgtcaaa atagggcaat cacctaatgt atatcaagct aaatttgaat    540
cggtggcatg gtcagcaaca gcatgccatg atggaaaaaa atggatgaca gttggagtca    600
cagggcccga caatcaagca attgcagtag tgaactatgg aggtgttccg gttgatatta    660
ttaattcatg ggcaggggat atttttaagaa cccaagaatc atcatgcacc tgcattaaag    720
gagactgtta ttgggtaatg actgatggac cggcaaatag gcaagctaat tataggatat    780
tcaaagcaaa agatggaaga gtaattggac gaactgatat aagtttcaat gggggacaca    840
tagaggagtg ttcttgttac cccaatgaag ggaaggtgga atgcatatgc agagacaatt    900
ggactggaac aaaatagacca attctggtaa tatcttctga tctatcgtac acagttggat    960
atttgtgtgc tggcattccc actgacaccc ctaggggaga ggatagtcaa ttcacaggct   1020
catgtacaag tcctttggga aataaaggat acggagtcaa aggtttcggg tttcgacaag   1080
gaactgacgt atgggccgga aggacaatta gtaggacttc aagatcagga ttcgaaataa   1140
taaaaatcag gaatggttgg acacagaata gtaaggacca atcaggagg caagtgatta   1200
tcgatgaccc aaattggtca ggatatagcg gttctttcac attgccggtt gaattaacaa   1260
aaaaaggatg tttggtcccc tgtttctggg ttgaaatgat tagaggtaaa cctgaagaaa   1320
caacaatatg gacctctagc agctccattg tgatgtgtgg agtagatcat aaaattgcca   1380
gttggtcatg gcacgatgga gcaattcttc cctttgacat cgataagatg taatttatga   1440
aaaaaactcc ttgtttctac t                                              1461
```

```
<210> SEQ ID NO 12
<211> LENGTH: 470
<212> TYPE: PRT
<213> ORGANISM: Influenza A virus (H3N8)

<400> SEQUENCE: 12
```

```
Met Asn Pro Asn Gln Lys Ile Ile Ala Ile Gly Ser Ala Ser Leu Gly
1               5                   10                  15

Ile Leu Ile Ile Asn Val Ile Leu His Val Val Ser Ile Ile Val Thr
            20                  25                  30

Val Leu Val Leu Asn Asn Asn Arg Thr Asp Leu Asn Cys Lys Gly Thr
        35                  40                  45

Ile Ile Arg Glu Tyr Asn Glu Thr Val Arg Val Glu Lys Leu Thr Gln
    50                  55                  60

Trp Tyr Asn Ile Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Glu Cys Arg
        115                 120                 125
```

```
Thr Phe Phe Leu Thr Gln Gly Ser Leu Leu Asn Asp Lys His Ser Asn
    130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Lys Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Asn Tyr Arg Ile Phe Lys Ala
                245                 250                 255

Lys Asp Gly Arg Val Ile Gly Arg Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Met
465                 470

<210> SEQ ID NO 13
<211> LENGTH: 1027
<212> TYPE: DNA
<213> ORGANISM: Influenza A virus (H3N8)

<400> SEQUENCE: 13
agcaaaagca ggtagatatt taaagatgag tcttctaacc gaagtcgaaa cgtacgttct     60
ctctatcata ccatcaggcc ccctcaaagc cgagatcgcg cagagacttg aagatgtctt    120
tgcgggaaag aacaccgatc ttgaggcact tatggaatgg ctaaagacaa gaccaatcct    180
```

```
gtcacctctg actaaaggga ttttaggatt tgtattcacg ctcaccgtgc ccagtgagcg    240
aggactgcag cgtagacgct ttgtccaaaa tgcccttagt ggaaacggag atccaaacaa    300
catggacaga gcagtaaaac tatacaggaa gcttaaaaga gaaataacat tccatggggc    360
aaaagaagtg gcactcagct attccactgg tgcactagcc agttgcatgg gactcatata    420
caacagaatg ggaactatta caaccgaagt ggcatttggc ctggtatgcg ccacatgtga    480
acagattgct gattcccagc atcggtctca caggcagatg gtgacaacaa ccaacccatt    540
aatcagacat gaaaacagaa tggtattagc cagcaccacg gctaaagcca tggaacagat    600
ggcaggatcg agtgagcaag cagcagaggc catggaggtt gctagtaggg ctaggcagat    660
ggtacaggca atgagaacca ttgggaccca ccctagctcc agtgccggtt tgaaagatga    720
tctccttgaa aatttacagg cctaccagaa acggatggga gtgcaaatgc agcgattcaa    780
gtgatcctct cgttactgca gcaagtatca ttgggatctt gcacttgata ttgtggattc    840
ttgatcgtct tttcttcaaa ttcatttatc gtcgccttaa atacgggtta aaaagagggc    900
cttctacgga aggagtacct gagtctatga gggaagaata tcggcaggaa cagcagaatg    960
ctgtggatgt tgacgatggt cattttgtca acatagagct ggagtaaaaa actaccttgt   1020
ttctact                                                              1027
```

```
<210> SEQ ID NO 14
<211> LENGTH: 252
<212> TYPE: PRT
<213> ORGANISM: Influenza A virus (H3N8)

<400> SEQUENCE: 14

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Ile Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
```

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
            245                 250

<210> SEQ ID NO 15
<211> LENGTH: 91
<212> TYPE: PRT
<213> ORGANISM: Influenza A virus (H3N8)

<400> SEQUENCE: 15

Met Ser Leu Leu Thr Glu Val Glu Thr Glu Cys Lys Cys Ser Asp Ser
1               5                   10                  15

Ser Asp Pro Leu Val Thr Ala Ala Ser Ile Ile Gly Ile Leu His Leu
            20                  25                  30

Ile Leu Trp Ile Leu Asp Arg Leu Phe Phe Lys Phe Ile Tyr Arg Arg
        35                  40                  45

Leu Lys Tyr Gly Leu Lys Arg Gly Pro Ser Thr Glu Gly Val Pro Glu
    50                  55                  60

Ser Met Arg Glu Glu Tyr Arg Gln Glu Gln Gln Asn Ala Val Asp Val
65                  70                  75                  80

Asp Asp Gly His Phe Val Asn Ile Glu Leu Glu
            85                  90

<210> SEQ ID NO 16
<211> LENGTH: 890
<212> TYPE: DNA
<213> ORGANISM: Influenza A virus (H3N8)

<400> SEQUENCE: 16
agcaaaagca gggtgacaaa aacataatgg attccaacac tgtgtcaagc tttcaggtag        60
actgttttct ttggcatgtc cgcaaacaat tcgcagacca agaactgggt gatgccccat       120
tccttgaccg gcttcgccga gaccagaagt ccctaagggg aagaggtagc actcttggtc       180
tggacatcga acagccact catgcaggaa agcagatagt ggagcagatt ctggaaaagg        240
aatcagatga ggcacctaaa atgaccattg cctctgttcc tgcttcacgc tacttaactg       300
acatgactct tgatgagatg tcaagagact ggttcatgct catgcccaag caaaagtaa        360 caggctccct atgtataaga atggaccagg caatcatgga taagaacatc atacttaaag       420
caaactttag tgtgattttc gaaaggctgg aaacactaat actcttaga gccttcaccg        480 aagaaggagc aatcgttggc gaaatttcac cattaccttc tcttccagga catactaatg       540
aggatgtcaa aaatgcaatt ggggtcctca tcggaggatt taaatggaat gataatacgg       600
ttaaaatctc tgaaactcta cagagattcg cttggagaag cagtcatgag aatgggagac       660
cttcactccc ttcaaagcag aaacgaaaaa tggagagaac aattaagcca gaaatttgaa       720
gaaataagat ggttgattga agaagtgcga catagactga aaaatacaga aaatagtttt       780
gaacaaataa catttatgca agccttacaa ctattgcttg aagtagaaca agagataaga       840
actttctcgt tcagcttat ttaatgataa aaaacacccct tgtttctact                  890

<210> SEQ ID NO 17
<211> LENGTH: 230
<212> TYPE: PRT
<213> ORGANISM: Influenza A virus (H3N8)

<400> SEQUENCE: 17

```
Met Asp Ser Asn Thr Val Ser Ser Phe Gln Val Asp Cys Phe Leu Trp
1               5                   10                  15

His Val Arg Lys Gln Phe Ala Asp Gln Glu Leu Gly Asp Ala Pro Phe
                20                  25                  30

Leu Asp Arg Leu Arg Arg Asp Gln Lys Ser Leu Arg Gly Arg Gly Ser
            35                  40                  45

Thr Leu Gly Leu Asp Ile Glu Thr Ala Thr His Ala Gly Lys Gln Ile
50                  55                  60

Val Glu Gln Ile Leu Glu Lys Glu Ser Asp Glu Ala Pro Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
                100                 105                 110

Gly Ser Leu Cys Ile Arg Met Asp Gln Ala Ile Met Asp Lys Asn Ile
            115                 120                 125

Ile Leu Lys Ala Asn Phe Ser Val Ile Phe Glu Arg Leu Glu Thr Leu
130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Phe Lys Trp Asn Asp Asn Thr Val
            180                 185                 190

Lys Ile Ser Glu Thr Leu Gln Arg Phe Ala Trp Arg Ser Ser His Glu
            195                 200                 205

Asn Gly Arg Pro Ser Leu Pro Ser Lys Gln Lys Arg Lys Met Glu Arg
210                 215                 220

Thr Ile Lys Pro Glu Ile
225                 230

<210> SEQ ID NO 18
<211> LENGTH: 121
<212> TYPE: PRT
<213> ORGANISM: Influenza A virus (H3N8)

<400> SEQUENCE: 18

Met Asp Ser Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Ile
                20                  25                  30

Ile Arg Leu Lys Ser Leu Lys Leu Tyr Arg Asp Ser Leu Gly Glu Ala
            35                  40                  45

Val Met Arg Met Gly Asp Leu His Ser Leu Gln Ser Arg Asn Glu Lys
50                  55                  60

Trp Arg Glu Gln Leu Ser Gln Lys Phe Glu Glu Ile Arg Trp Leu Ile
65                  70                  75                  80

Glu Glu Val Arg His Arg Leu Lys Asn Thr Glu Asn Ser Phe Glu Gln
                85                  90                  95

Ile Thr Phe Met Gln Ala Leu Gln Leu Leu Leu Glu Val Glu Gln Glu
                100                 105                 110

Ile Arg Thr Phe Ser Phe Gln Leu Ile
            115                 120
```

SINGLE-CYCLE VIRUS FOR THE DEVELOPMENT OF CANINE INFLUENZA VACCINES

CROSS-REFERENCES TO RELATED APPLICATIONS

This application is a U.S. national phase application filed under 35 U.S.C. § 371 claiming benefit to International Patent Application No. PCT/US16/47726, filed Aug. 19, 2016, which is entitled to priority under 35 U.S.C. § 119(e) to U.S. Provisional Patent Application No. 62/207,579, filed Aug. 20, 2015, each of which application is hereby incorporated herein by reference in its entirety.

BACKGROUND OF THE INVENTION

Canine influenza virus (CIV) is a recently emerged virus that causes acute respiratory disease in dogs. CIV was first isolated in 2004 from racing greyhound dogs during a respiratory disease outbreak at a Florida racetrack. Subsequently outbreaks were reported at greyhound racetracks and among other breeds of pet dogs. The H3N8 CIV resulted from the transfer of H3N8 equine influenza virus (EIV) to dogs around 1999. These findings were surprising as dogs were thought to be refractory to infection with influenza viruses. Most dogs have no immunity to CIV and infection may therefore spread quickly in any location with concentrated dog populations. Pet dogs are the most popular companion animals living with humans, and may support the replication of multiple influenza virus subtypes and could facilitate the generation of novel virus species with pandemic potential for humans. The true risk of human infection by CIV is unknown as we do not understand the host barriers that restrict human infection.

CIV H3N2 has been previously found in dogs in China, Korea and Thailand, where it has been circulating since it emerged in late 2005. The H3N2 CIV has been recently introduced (2015) in the USA, most likely through the transport of infected rescue dogs from Korea and is now spreading widely in the mid-Western states. This raise concerns about exposure of human in this country, as well as the likely generation of natural reassortants with the H3N8 CIV.

In 2006, the American Veterinary Medical Association (AVMA) called for the urgent development of an effective vaccine against CIV. A vaccine made from inactivated virus have been developed that is administered subcutaneously as two doses to reduce the severity of the CIV disease and to reduce the incidence of CIV infection in naive dogs (Nobivac, Merck). However, to date, no LAIV for CIV infections has been developed. Thus there is a need in the art for improved vaccines for CIV. The present invention satisfies this unmet need.

SUMMARY OF THE INVENTION

In one aspect, the present invention provides an immunological composition comprising a single-cycle infectious canine influenza virus (sciCIV), wherein the sciCIV comprises one or more mutations in segment 4 of the viral genome.

In one embodiment, the one or more mutations in segment 4 results in the lack of expression of HA. In one embodiment, the one or more mutations in segment 4 comprises the deletion of at least a portion of nucleotide sequence encoding HA. In one embodiment, the one or more mutation comprises the deletion of the whole nucleotide sequence encoding HA.

In one embodiment, the sciCIV is derived from H3N8 subtype of influenza A virus. In one embodiment, the composition is used for the treatment or prevention of canine influenza in a subject.

In one aspect, the present invention provides a method for treating or preventing canine influenza in a subject. The method comprises administering to the subject an immunological composition comprising a single-cycle infectious canine influenza virus (sciCIV), wherein the sciCIV comprises one or more mutations in segment 4 of the viral genome.

In one embodiment, the one or more mutations in segment 4 results in the lack of expression of HA. In one embodiment, the one or more mutations in segment 4 comprises the deletion of at least a portion of nucleotide sequence encoding HA. In one embodiment, the one or more mutation comprises the deletion of the whole nucleotide sequence encoding HA.

In one embodiment, the sciCIV is derived from H3N8 subtype of influenza A virus.

In one embodiment, the composition is used for the treatment or prevention of canine influenza in a subject. In one embodiment, the subject does not have canine influenza, and wherein the method induces immunity against one or more of: influenza A virus subtype H3N8 and influenza A virus subtype H3N2. In one embodiment, the subject is infected with at least one or more of: influenza A virus subtype H3N8 and influenza A virus subtype H3N2; and wherein the method induces a therapeutic immune response.

In one embodiment, the immunological composition is administered intranasally, intratracheally, orally, intradermally, intramuscularly, intraperitoneally, intravenously, or subcutaneously. In one embodiment, the subject is a dog.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A) HA protein detection by indirect immunofluorescence: Parental and HA-expressing influenza A/Puerto Rico 8/34 H1N1 (PR8) and A/canine/NY/dog23/2009 H3N8 (CIV) MDCK cells were fixed and stained with a PR8 anti-HA monoclonal antibody (PY102) or with a CIV anti-HA polyclonal antibody (NR-3103) and counterstained with DAPI to visualize the cell nuclei. Representative images obtained with a ×20 objective are shown. Bars, 50 μm. FIG. 1B) HA protein detection by Western blot: Parental and HA-expressing PR8 and CIV MDCK whole cell lysates were incubated with the PR8 anti-HA monoclonal antibody PY102 or the CIV anti-HA polyclonal NR-3103. A monoclonal antibody against actin was used as a loading control. The HA0 and HA1 are indicated with white or black arrows, respectively.

FIG. 2, comprising FIG. 2A through FIG. 2C, depicts the results of example experiments demonstrating the generation and characterization of sciCIV. FIG. 2A) Schematic representation of the recombinant GFP vRNA-like segment. The GFP vRNA-like segment contains the GFP open reading frame flanked by the terminal untranslated regions (thin black lines), along with the HA packaging signals (gray boxes), which are required for efficient incorporation of the GFP vRNA-like into the virus particle. Multicycle growth analysis of sciCIV in parental and HA-expressing MDCK cells. Confluent monolayers of parental and PR8 or CIV HA-expressing MDCK cells were infected (12-well plate format, triplicates) with the sciCIV at a low multipliciry of infection, MOI (0.001). At the indicated times post-infection (24, 48 and 72 h), GFP was visualized by fluorescence microscopy using a ×20 objective (FIG. 2B). Tissue culture supernatants at the same times post-infection were collected for sciCIV titration in MDCK-HA cells. Data represent the means±SDs of the results determined in triplicate. Dotted black line, limit of detection (200 FFU/ml) (FIG. 2C).

FIG. 4, comprising FIG. 4A and FIG. 4B, depicts the results of experiments evaluating the induction of humoral responses by sciCIV vaccination. Female 6-to-8-week-old C57BL/6 mice were immunized with the CIV inactivated vaccine (Nobivac; 100 ul intramuscular) or with $1 \times 10^3$ FFU of A/canine/NY/dog23/2009 H3N8 CIV wild-type (WT), $1 \times 10^5$ FFU of sciCIV that was (sciCIV-UV) or was not (sciCIV) exposed to UV light on ice for 20 min (FIG. 4A); or mock vaccinated with PBS intranasally. At 14 days post-infection, mice were bled and the sera were collected and evaluated by ELISA for IgG antibodies against total viral proteins using cell extracts of MDCK cells infected with A/canine/NY/dog23/2009 H3N8 CIV WT (FIG. 4B). Mock-infected cell extracts were used to evaluate the specificity of the antibody response. OD, optical density. Data represent the means+/−SDs of the results for 4 individual mice.

DETAILED DESCRIPTION

Figure 1B:
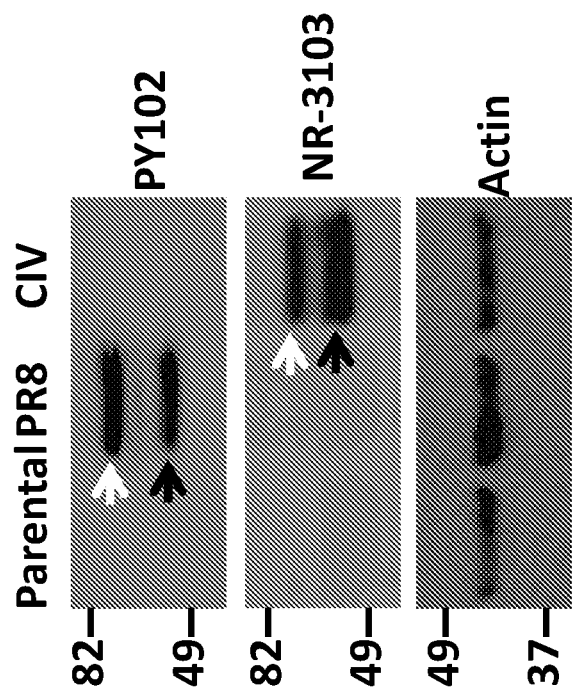
FIG. 1A and FIG. 1B, depicts the results of experiments demonstrating the generation and characterization of CIV (A/canine/NY/dog23/2009 H3N8) HA-expressing MDCK cells.

The present invention relates to compositions and methods for the treatment and prevention of canine influenza virus (CIV) and CIV-related pathology. The present invention is based in part upon the discovery that one or more mutations in segment 4 of the viral genome produces a single cycle infectious CIV (sciCIV). The sciCIV does not allow for the production of infectious progeny, but is able to induce a CIV-specific immune response. In certain embodiments, the sciCIV is a live-attenuated CIV (LACIV).

In certain embodiments, the present invention provides a composition for the treatment and prevention of canine influenza virus (CIV) and CIV-related pathology. In one embodiment, the composition comprises a sciCIV having one or more mutations in segment 4, which natively encodes for HA protein. For example, in one embodiment, the sciCIV comprises a deletion mutant in segment 4, which results in the lack of HA expression.

In certain embodiments, the present invention provides a method for treating or preventing CIV and CIV-related pathology, comprising administering a composition comprising a LACIV. In certain embodiments, the method comprises intranasal delivery of the LACIV.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles “a” and “an” are used herein to refer to one or to more than one (i.e., to at least one) of the grammatical object of the article. By way of example, “an element” means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "normal temperature" or "normal body temperature" as used herein refers to the temperature of a healthy subject. For example, in certain instances the "normal body temperature" in a human subject is in the range of about 36° C. to about 38° C. In certain instances, in a canine subject, "normal body temperature" is in the range of about 38° C. to about 39.5° C.

The term "elevated temperature" or "elevated body temperature" as used herein refers to a temperature in a subject that is greater than the "normal body temperature" of a subject of a given organism. In certain instances "elevated body temperature" may be indicative of a fever, infection, or other illness. In certain instances, elevated body temperature in a human subject is greater than about 37° C. In certain instances, elevated body temperature in a canine subject is greater than about 38.5° C.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides immunological compositions and methods useful for the inhibition, prevention and treatment of canine influenza and canine influenza related diseases and disorders. In one embodiment, the immunological composition comprises a live-attenuated virus (LAV).

In one embodiment, the present invention provides a single-cycle infectious virus of a canine influenza virus. For example, it is demonstrated herein that one or more mutations in segment 4 of the CIV genome produces a sciCIV. The sciCIV of the present invention is unable to produce infectious progeny. However, the sciCIV provides antigen-specific immune responses and protection against CIV. In one embodiment, the sciCIV provides at least the same antigen-specific immune responses and protection against CIV compared to wildtype CIV. In certain embodiments, the sciCIV provides greater antigen-specific immune responses and protection against CIV as compared to inactivated CIV.

In general, wild-type influenza viruses contain a segmented genome with 8 segments as described in Table 1 below:

TABLE 1

| Segment | Gene Product |
| --- | --- |
| 1 | PB2 (Polymerase (basic) protein 2) |
| 2 | PB1 (Polymerase (basic) protein 1) |
| 3 | PA (Polymerase (acidic) protein) |
| 4 | HA (Hemagglutinin) |
| 5 | NP (Nucleoprotein) |
| 6 | NA (Neuraminidase) |
| 7 | M1 (Matrix protein 1) and M2 (Matrix protein 2) |
| 8 | NS1 (non-structural protein 1) and NEP/NS2 (non-structural protein 2) |

In certain embodiments, the present invention provides an immunological composition comprising segment 4, wherein segment 4 comprises one or more mutations. For example, in certain embodiments, the immunological composition comprises a sciCIV, comprising one or more mutations in segment 4. In one embodiment, the immunological composition comprises a sciCIV, comprising a deletion mutant in segment 4 resulting in the lack of HA expression.

The present invention also provides methods of preventing, inhibiting, and treating CIV and CIV-related diseases and disorders. In one embodiment, the methods of the invention induce immunity against CIV by generating an immune response directed to CIV. In one embodiment, the methods of the invention induce production of CIV-specific antibodies. In one embodiment, the methods of the invention prevent CIV-related pathology. In one embodiment, the methods of the invention comprise administering an immunological composition comprising a sciCIV, wherein the sciCIV comprises one or more mutations in segment4, to a subject in need thereof. In one embodiment, the methods comprise administering an immunological composition to a subject in need thereof, thereby inducing immunity to CIV.

Compositions

The present invention provides immunological compositions that when administered to a subject in need thereof, elicit an immune response directed against canine influenza virus (CIV). In some embodiments, the composition includes polypeptides, nucleotides, vectors, or vaccines. Further, when the compositions are administered to a subject, they elicit an immune response that serves to protect the inoculated subject against canine influenza. As exemplified herein, the composition can be obtained in large quantities for use as a vaccine.

In one embodiment, the present invention provides compositions that are useful as immunomodulatory agents, for example, in stimulating immune responses and in preventing canine influenza and canine influenza-related pathology.

In one embodiment, the composition is a mutant CIV that induces an anti-CIV immune response. In one embodiment, the mutant CIV is a sciCIV comprising one or more mutations in segment 4. For example, in one embodiment, the sciCIV comprises a deletion mutant in segment 4, such that the sciCIV does not express HA. In one embodiment, the deletion mutant of segment 4 is lacking at least a portion of the nucleotide sequence that encodes HA. In one embodiment, the deletion mutant of segment 4 is lacking the entirety of the nucleotide sequence that encodes HA. In one embodiment, segment 4 of the sciCIV comprises HA packing signals (see FIG. 2). In certain embodiments, the sciCIV is unable to produce infectious progeny, but is still able to induce an anti-CIV immune response. In certain embodiments, the sciCIV is a live-attenuated CIV (LACIV).

In one embodiment, the sciCIV is based upon the genome of Influenza A/canine/NY/dog23/2009 H3N8. Wildtype nucleic acid sequences for each segment of Influenza A/canine/NY/dog23/2009 H3N8 and wildtype amino acid sequences for the encoded proteins are summarized in Table 2 below:

TABLE 2

Wildtype sequences for Influenza A/canine/NY/dog23/2009 H3N8

| Segments | Gene Products |
| --- | --- |
| Segment 1 (SEQ ID NO: 1) | PB2 (SEQ ID NO: 2) |
| Segment 2 (SEQ ID NO: 3) | PB1 (SEQ ID NO: 4) |
| Segment 3 (SEQ ID NO: 5) | PA (SEQ ID NO: 6) |
| Segment 4 (SEQ ID NO: 7) | HA (SEQ ID NO: 8) |
| Segment 5 (SEQ ID NO: 9) | NP (SEQ ID NO: 10) |
| Segment 6 (SEQ ID NO: 11) | NA (SEQ ID NO: 12) |
| Segment 7 (SEQ ID NO: 13) | M1 (SEQ ID NO: 14)  M2 (SEQ ID NO: 15) |
| Segment 8 (SEQ ID NO: 16) | NS1 (SEQ ID NO: 17)  NEP/NS2 (SEQ ID NO: 18) |

In one embodiment, the composition comprises one or more mutations in the nucleic acid sequences of segment 4, which, in wildtype CIV, encodes HA. Thus, in certain embodiments, the composition comprises a deletion mutant of segment 4, where HA is not expressed. As described herein, the mutation of segment 4 produces a sciCIV that is unable to produce infectious progeny, but is able to induce an immune response.

In one embodiment, the sciCIV comprises segment 4 having HA packaging signals. For example, in certain embodiments, the mutant segment 4 of the sciCIV comprises packaging signals at its 5' (80 nucleotides) and 3' (45 nucleotides) ends. In certain embodiments, the mutant segment 4 comprises 5' and 3' untranslated regions (UTRs). In certain embodiments, mutant segment 4 comprises a nucleotide sequence encoding a marker protein. Exemplary marker proteins include, but are not limited to GFP, eGFP, YFP, RFP, CFP, luciferase, beta-galactosidase, and the like. For example, in certain embodiments, a nucleotide sequence encoding the marker protein replaces the nucleotide sequence encoding HA.

In one embodiment, the composition comprises nucleotide sequence that is substantially homologous to a nucleotide sequence described herein. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to a nucleotide sequence described herein.

In certain embodiments, the composition comprises one or more mutations in the nucleic acid sequences of segment 4, while comprising wildtype nucleic acid sequences for the rest of the segmented genome. For example, in one embodiment, the sciCIV comprises one or more mutations in segment 4 and comprises wildtype segment 1, segment 2, segment 3, segment 5, segment 6, segment 7, and segment 8.

In certain embodiments, the composition comprises one or more mutations in segment 4, in combination with one or more mutations in one or more other segments of the viral genome.

For example, in one embodiment, the composition further comprises one or more mutations in segment 8. In one embodiment, the composition comprises a deletion mutant of segment 8, such that the coding region of NS1 protein is truncated or deleted, as described in PCT Patent Application PCT/US2016/47711, filed on Aug. 19, 2016, claiming priority to U.S. Provisional Patent Application No. 62/207,576, each of which applications are incorporated by reference in their entirety.

In one embodiment, the composition further comprises one or more mutations in segment 1 and/or segment 2. In one embodiment, the composition comprises a mutation in segment 1 and/or segment 2, encoding a point mutation in PB2 and/or PB1 that render the CIV temperature sensitive. An exemplary point mutations of PB2 is N265S. Exemplary point mutations of PB1 include a K391E point mutation, a E581G point mutation, and a A661T point mutation, as described in PCT Patent Application PCT/US2016/47715, filed on Aug. 19, 2016, claiming priority to U.S. Provisional Patent Application No. 62/207,571, each of which applications are incorporated by reference in their entirety.

In certain embodiments, the composition comprises a polynucleotide comprising a deletion mutation of segment 4. The polynucleotide can be RNA or DNA. In one embodiment, the composition comprises a DNA vaccine.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid comprising a nucleotide sequence having substantial homology to a nucleotide sequence of an isolated nucleic acid encoding a polypeptide disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass a RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

According to yet another embodiment, composition of the invention, comprising the nucleic acid sequences or combination of nucleic acid sequences of the present invention, is capable of generating a CIV-specific immune response. In another embodiment, the composition of the invention, comprising the nucleic acid sequences or combination of nucleic acid sequences of the present invention, is capable of generating CIV-specific antibodies. In certain embodiments, the composition is able to protect against CIV, including H3N8 CIV and H3N2 CIV.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, composition of the invention, comprising the polypeptide or combination of polypeptides of the present invention, is capable of generating a CIV-specific immune response. In another embodiment, the composition of the invention, comprising the polypeptide or combination of polypeptides of the present invention, is capable of generating CIV-specific antibodies. In certain embodiments, the composition is able to protect against CIV, including H3N8 CIV and H3N2 CIV.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

Mutant Viruses

The invention relates in part to the generation, selection and identification of mutant CIV that generate a CIV-specific immune response, and the use of such viruses in vaccine and pharmaceutical formulations. In one embodiment, the mutant virus is a sciCIV. In one embodiment, the mutant virus is a LACIV.

As described herein, in certain embodiments the mutant virus comprises one or more mutations in segment 4. For example, in one embodiment, the mutant virus comprises a deletion mutant of segment 4, where the mutant virus does not express HA. In one embodiment, the mutant virus is unable to produce infectious progeny. However, the mutant virus induces CIV-specific immune responses and antibody production, and is thus able to protect against CIV and CIV-related pathology.

Any mutant virus or strain which has at least one mutation can be selected and used in accordance with the invention. In one embodiment, naturally occurring mutants or variants, or spontaneous mutants can be selected that include at least one mutation in segment 4, as described elsewhere herein. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having at least one mutation in segment 4, as described elsewhere herein. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into an influenza virus, including, but not limited to H3N8 CIV or H3N2 CIV using "reverse genetics" approaches. In this way, natural or other mutations which confer the attenuated phenotype can be engineered into vaccine strains. For example, deletions, insertions, or substitutions of the coding region of segment 4, encoding HA, can be engineered. Deletions, substitutions or insertions in the non-coding region of segment 4 are also contemplated. To this end, mutations in the signals responsible for the transcription, replication, polyadenylation and/or packaging of segment 4 can be engineered.

In certain instances, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. In some instances, a more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain.

In an alternate embodiment, a combination of reverse genetics techniques and reassortant techniques can be used to engineer attenuated viruses having the desired epitopes. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

The attenuated virus of the present invention can itself be used as the active ingredient in vaccine or pharmaceutical formulations. In certain embodiments, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens.

For example, in one embodiment, the immunological composition of the invention comprises a mutant virus, engineered to express one or more epitopes or antigens of CIV along with epitopes or antigens of another pathogen. For example, the mutant virus can be engineered to express neutralizing epitopes of other preselected strains. Alternatively, epitopes of other viruses can be built into the mutant virus. Alternatively, epitopes of non-viral infectious pathogens (e.g., parasites, bacteria, fungi) can be engineered into the virus.

In one embodiment, the mutant viruses selected for use in the invention is capable of inducing a robust anti-CIV response in the host—a feature which contributes to the generation of a strong immune response when used as a vaccine, and which has other biological consequences that make the viruses useful as pharmaceutical agents for the prevention and/or treatment of other viral infections, or other diseases.

The viruses, which induce a CIV-specific immune response in hosts, may also be used in pharmaceutical formulations for the prophylaxis or treatment of other influenza infections, or influenza-related pathology. In this regard, the tropism of the attenuated virus can be altered to target the virus to a desired target organ, tissue or cells in vivo or ex vivo. Using this approach, the CIV-specific immune response can be induced locally, at the target site, thus avoiding or minimizing the side effects of systemic treatments. To this end, the attenuated virus can be engineered to express a ligand specific for a receptor of the target organ, tissue or cells.

Vaccine

In certain aspects, the immunological composition is useful as a vaccine, where the immunological composition induces an immune response to the antigen in a cell, tissue or mammal. Preferably, the vaccine induces a protective immune response in the mammal. As used herein, an "immunological composition" may comprise, by way of examples, a virus, a mutant virus, a single-cycle infectious virus, a live-attenuated virus (LAV), an antigen (e.g., a polypeptide), a nucleic acid encoding an antigen (e.g., an antigen expression vector), or a cell expressing or presenting an antigen or cellular component. In particular embodiments the immunological composition comprises or encodes all or part of any polypeptide antigen described herein, or an immunologically functional equivalent thereof. In other embodiments, the immunological composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces anti-CIV immunity or suppresses CIV upon inoculation into an animal.

The invention encompasses vaccine formulations comprising a mutant CIV. For example, in one embodiment, the mutant CIV is a sciCIV. For example, in certain embodiments, the sciCIV is unable to produce infectious progeny. In one embodiment, the vaccine comprises a sciCIV comprising one or more mutations in segment 4, and a suitable excipient. The virus used in the vaccine formulation may be selected from naturally occurring mutants or variants, mutagenized viruses or genetically engineered viruses. Mutant strains of CIV can also be generated via reassortment techniques, or by using a combination of the reverse genetics approach and reassortment techniques. Naturally occurring variants include viruses isolated from nature as well as spontaneous occurring variants generated during virus propagation. The mutant virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

In one embodiment, the vaccine formulation comprises a plurality of mutant CIV. For example, in one embodiment, the vaccine formulation may comprise one or more of the sciCIV, described herein, in combination with other mutant CIV that induce an anti-CIV immune response. For example, in one embodiment, the vaccine formulation comprises a live-attenuated CIV having one or more mutations in segment 1 and/or segment 2. In one embodiment, the vaccine formulation comprises a mutant CIV comprising a deletion mutant in segment 8.

In one embodiment, the present invention comprises a method of generating a mutant CIV, comprising contacting a host cell with a polynucleotide comprising the nucleic acid sequences of segment 4, having one or more mutations, described elsewhere herein.

Propagation of the virus in culture is known to persons in the art. Briefly, the virus is grown in the media compositions in which the host cell is commonly cultured. Suitable host cells for the replication of CIV include, e.g., Vero cells, BHK cells, MDCK cells, 293 cells COS cells, and CEK cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, 5th ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of a virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Many methods may be used to introduce the vaccine formulations described above, these include but are not limited to introduction intranasally, intratracheally, orally, intradermally, intramuscularly, intraperitoneally, intravenously, and subcutaneously. It may be preferable to introduce the virus vaccine formulation via the natural route of infection of the pathogen for which the vaccine is designed, or via the natural route of infection of the parental attenuated virus.

A vaccine of the present invention, comprising a mutant CIV, for example a sciCIV, could be administered once. Alternatively, a vaccine of the present invention, comprising a mutant CIV, could be administered twice or three or more times with a suitable interval between doses. Alternatively, a vaccine of the present invention, comprising a mutant CIV, could be administered as often as needed to an animal, preferably a mammal.

Methods

The invention provides a method for treating or preventing canine influenza infection or a CIV-related disease or disorder. In one embodiment, the method comprises administering an immunological composition comprising a mutant CIV. In one embodiment, the method comprises administering an immunological composition comprising a mutant CIV comprising one or more mutations in segment 4, to a subject in need thereof. In one embodiment, the mutant CIV is a sciCIV.

In certain embodiments, the mutant CIV induces an enhanced immune response as compared to an inactivated CIV. For example, in certain embodiments, the induced immune response of LACIV is 2-fold more, 3-fold more, 5-fold more, 10-fold more, 15-fold more, 20-fold more, 50-fold more, 100-fold more, 500-fold more, or 1000-fold more, than inactivated CIV. The immune response induced the mutant CIV can be measured using standard assays. For example, in certain embodiments, the immune response induced by mutant CIV is measured by detecting the amount of CIV-specific antibodies produced in the subject following administration of mutant CIV.

The therapeutic compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In certain embodiments, the subject is a mammal. For example, the subject may include, but is not limited to, a human, primate, cow, horse, sheep, pig, dog, cat, or rodent. In one embodiment, the subject is a dog. The method may be used to treat or prevent CIV or CIV-related pathology in any breed or species of dog. In certain embodiments, the relative amount of active ingredient in a single dose, or the frequency of doses, will vary depending on the age, sex, weight, or breed of subject (e.g. dog).

The composition may be combined with an adjuvant. An adjuvant refers to a compound that enhances the immune response when administered together (or successively) with the immunological composition. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering an immunological composition of the invention directly to a subject in need thereof. Administration of the composition can comprise, for example, intranasal, intramuscular, intravenous, peritoneal, subcutaneous, intradermal, as well as topical administration.

Furthermore, the actual dose and schedule can vary depending on whether the compositions are administered in combination with other pharmaceutical compositions, or depending on inter-individual differences in pharmacokinetics, drug disposition, and metabolism. One skilled in the art can easily make any necessary adjustments in accordance with the exigencies of the particular situation.

Pharmaceutical Compositions

The present invention envisions treating or preventing CIV or CIV-related pathology in a mammal by the administration of a therapeutic composition of the invention to a mammal in need thereof. Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention encompasses pharmaceutical compositions comprising a mutant CIV to be used as anti-viral agents or as agents against CIV-related diseases and disorders. The pharmaceutical compositions have utility as an anti-viral prophylactic and may be administered to a subject at risk of getting infected or is expected to be exposed to a virus. For example, subjects traveling to parts of the world where CIV is prevalent can be administered a pharmaceutical composition of the invention. In certain embodiments, subjects who are expected to be in contact with other subjects at risk, can be administered a pharmaceutical composition of the invention.

The mutant CIV of the invention may be engineered using the methods described herein to express proteins or peptides which would target the viruses to a particular site. In one embodiment, where the site to be targeted expresses a receptor to a growth factor, e.g., VEGF, EGF, or PDGF, the mutant CIV may be engineered to express the appropriate growth factor or portion(s) thereof. Thus, in accordance with the invention, the mutant CIV may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, the pharmaceutical composition is a veterinary pharmaceutical composition suitable for administration to a veterinary subject, including but not limited to a canine subject. Exemplary canine subjects include dogs, wolves, foxes, coyotes, and jackals.

In certain embodiments, the veterinary pharmaceutical composition is "palatable," meaning an oral veterinary composition that is readily accepted by canines, including dogs, without any coaxing or with some coaxing. Palatable compositions are compositions that score at least 2 using a palatability assessment method wherein dog owners score the composition from 0 to 3, wherein dogs scoring 0 do not consume the composition; dogs scoring 1 consume the composition after some time; dogs scoring 2 consume the composition with some coaxing and dogs scoring 3 consume the composition readily. A skilled person is well-versed in these palatability standards and scoring regimes. In another embodiment, the daily dose for dogs may be around 100 mg/kg. Veterinary pharmaceutical agents that may be included in the compositions of the invention are well-known in the art (see e.g. Plumb' Veterinary Drug Handbook, 5th Edition, ed. Donald C. Plumb, Blackwell Publishing, (2005) or The Merck Veterinary Manual, 9th Edition, (January 2005)).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment or prevention of a particular disease or disorder will depend on the nature of the disease or disorder, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Using plasmid-based reverse genetics techniques, a single-cycle infectious canine influenza virus (sciCIV) was developed based on the A/canine/NY/dog23/2009 H3N8 influenza virus. In this sciCIV approach, the fourth viral segment, which encodes for the receptor-binding and fusion protein hemagglutinin (HA), has been removed. Thus, upon infection of normal cells, although no infectious progeny are produced, the expression of other viral proteins occurs and is immunogenic. The nucleic acid sequences of the viral segments, and the amino acid sequences of the encoded viral proteins, used in the development of the sciCIV are provided in SEQ ID NOs: 1-18)

Figure 1A:
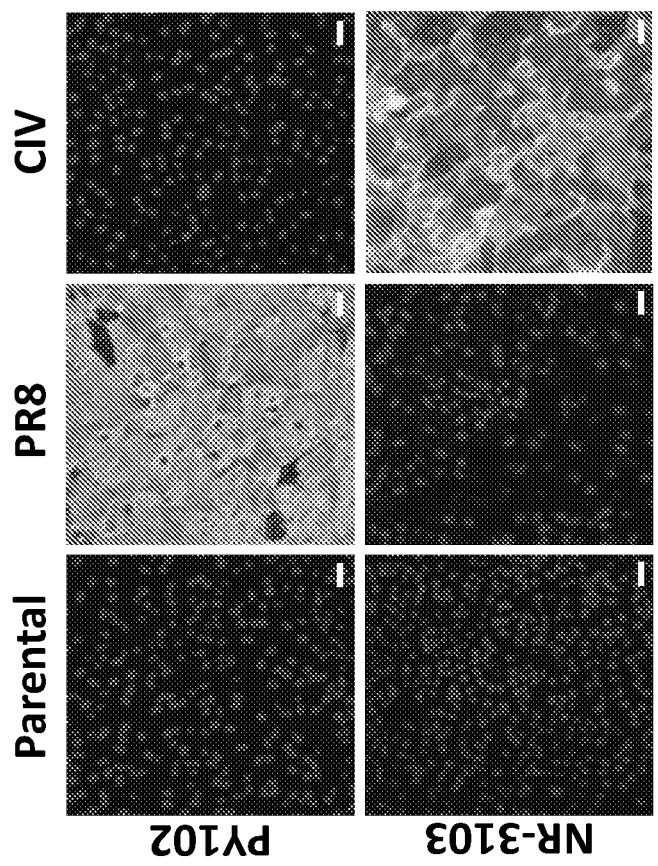

Experiments were first conducted to generate and characterize CIV (A/canine/NY/dog23/2009 H3N8) HA-expressing MDCK cells. HA protein was first detected by indirect immunofluorescence. Parental and HA-expressing influenza A/Puerto Rico 8/34 H1N1 (PR8) and A/canine/NY/dog23/2009 H3N8 (CIV) MDCK cells were fixed and stained with a PR8 anti-HA monoclonal antibody (PY102) or with a CIV anti-HA polyclonal antibody (NR-3103) and counterstained with DAPI to visualize the cell nuclei (FIG. 1A). HA protein was also detected by Western blot. Parental and HA-expressing PR8 and CIV MDCK whole cell lysates were incubated with the PR8 anti-HA monoclonal antibody PY102 or the CIV anti-HA polyclonal NR-3103 (FIG. 1B).

A single cycle infectious CIV (sciCIV) was generated. FIG. 2A depicts a schematic of the recombinant GFP vRNA-like segment. The GFP vRNA-like segment contains the GFP open reading frame flanked by the terminal untranslated regions (thin black lines), along with the HA packaging signals (gray), which are required for efficient incorporation of the GFP vRNA-like into the virus particle. Experiments investigating the multicycle growth of sciCIV in parental and HA-expressing MDCK cells was conducted. Confluent monolayers of parental and PR8 or CIV HA-expressing MDCK cells were infected (12-well plate format, triplicates) with the sciCIV at a low MOI (0.001). GFP was visualized at 24, 48, and 72 hours post-infection by fluorescence microscopy using a ×20 objective (FIG. 2B). Tissue culture supernatants at the same times post-infection were collected for sciCIV titration in MDCK-HA cells, which demonstrates that PR8 and CIV HA-expressing cells equally support sciCIV growth (FIG. 2C).

Figure 3:
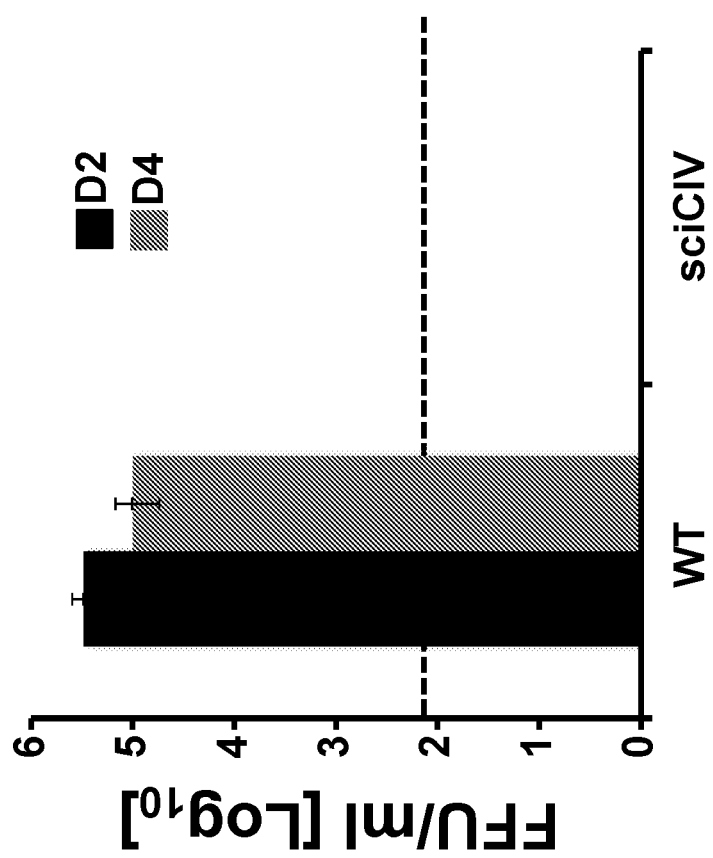
FIG. 3 depicts the results of experiments evaluating the attenuation of sciCIV. Female 6-to-8-week-old C57BL/6 mice (n=6) were infected intranasally with or with $1 \times 10^3$ Focus Forming Units (FFU) of CIV A/canine/NY/dog23/2009 H3N8 wild-type (WT) or $1 \times 10^5$ FFU of sciCIV. To evaluate viral lung replication, mice were sacrificed at days 2 (n=3) and 4 (n=3) post-infection and lungs were harvested, homogenized, and used to quantify viral titers by immunofocus assay (FFU/ml) using an anti-NP monoclonal antibody (HB-65). Data represent the means and SD. Dotted black lines indicate limit of detection (200 FFU/ml).

Experiments were conducted to evaluate the attenuation of sciCIV. Female 6-to-8-week-old C57BL/6 mice (n=6) were infected intranasally with or with $1 \times 10^3$ Focus Forming Units (FFU) of CIV A/canine/NY/dog23/2009 H3N8 wild-type (WT) or $1 \times 10^5$ FFU of sciCIV. To evaluate viral lung replication, mice were sacrificed at days 2 (n=3) and 4 (n=3) post-infection and lungs were harvested, homogenized, and used to quantify viral titers by immunofocus assay (FFU/ml) using an anti-NP monoclonal antibody (HB-65). It was observed that no detectable amount of sciCIV was present in the lungs post-infection (FIG. 3), highlighting the safety of the sciCIV approach.

Experiments were conducted to evaluate the induction of humoral responses by sciCIV vaccination. Female 6-to-8-week-old C57BL/6 mice were immunized with the CIV inactivated vaccine (Nobivac; 100 ul intramuscular) or with $1 \times 10^3$ FFU of A/canine/NY/dog23/2009 H3N8 CIV wild-type (WT), $1 \times 10^5$ FFU of sciCIV that was (sciCIV-UV) or was not (sciCIV) exposed to UV light on ice for 20 min (FIG. 4A); or mock vaccinated with PBS intranasally. At 14 days post-infection, mice were bled and the sera were collected and evaluated by ELISA for IgG antibodies against total viral proteins using cell extracts of MDCK cells infected with A/canine/NY/dog23/2009 H3N8 CIV WT. Mock-infected cell extracts were used to evaluate the specificity of the antibody response. It was observed that sciCIV was able to induce a CIV-specific immune response (FIG. 4B, Table 3).

TABLE 3

Immunogenicity of sciCIV

| Immunization and dose[a] | | Mean (SD) serum HAI titer[b] |
|---|---|---|
| PBS | — | ≤8 (ND) |
| WT | $10^3$ FFU | 215.3 (64) |
| sciCIV | $10^5$ FFU | 8 (0) |
| sciCIV-UV | $10^5$ FFU | ≤8 (ND) |
| Nobivac | 100 µl | 26.9 (8) |

Figure 5:
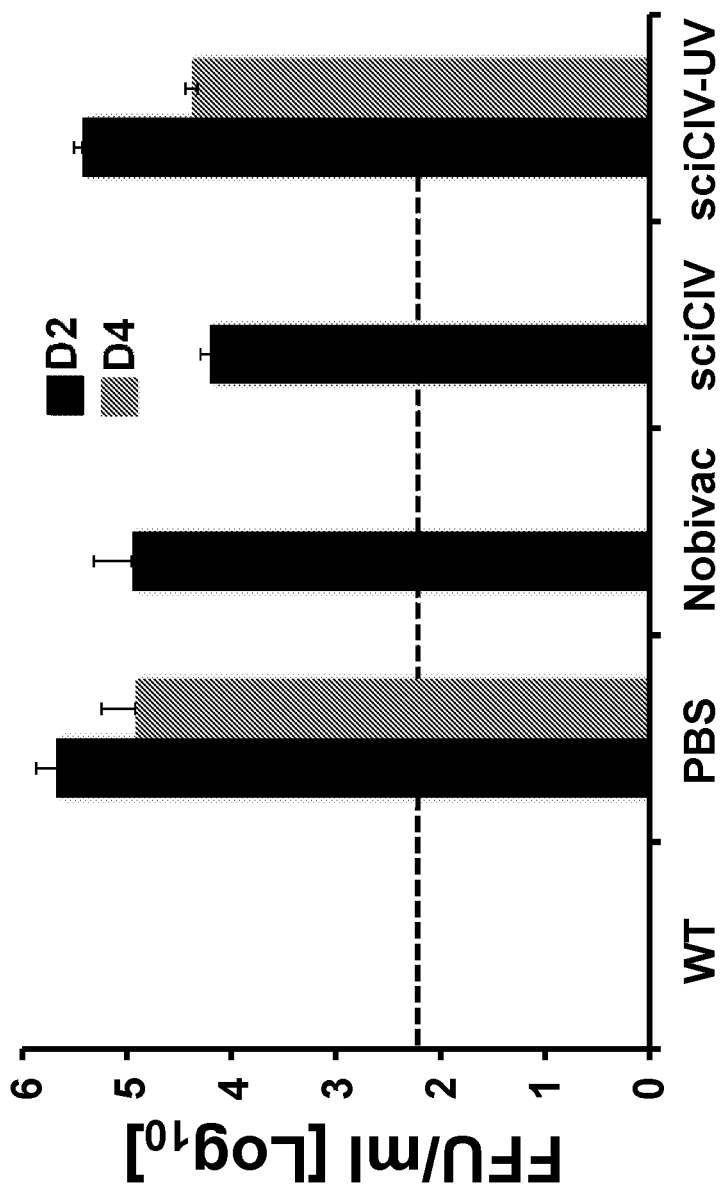
FIG. 5, depicts the results of example experiments evaluating the protection efficacy of sciCIV. Female 6-to-8-week-old C57BL/6 mice (n=6) were immunized with the CIV inactivated vaccine (Nobivac; 100 ul intramuscular), or with $1 \times 10^3$ FFU of A/canine/NY/dog23/2009 H3N8 CIV wild-type (WT), $1 \times 10^5$ FFU of sciCIV that was (sciCIV-UV) or was not (sciCIV) exposed to UV light on ice for 20 min; or mock vaccinated with PBS intranasally. Two weeks post-vaccination, mice were challenged with $1 \times 10^5$ FFU of A/canine/NY/dog23/2009 H3N8 CIV WT. To evaluate viral lung replication, mice were sacrificed at days 2 (n=3) and 4 (n=3) post-infection with A/canine/NY/dog23/2009 H3N8 CIV WT and lungs were harvested, homogenized, and used to quantify viral titers by immunofocus assay (FFU/ml) using an anti-NP monoclonal antibody (HB-65). Dotted black lines indicate limit of detection (200 FFU/ml). Data represent the means+/−SDs.

[a]Virus was administered intranasally to anesthetized mice (n = 4), Nobivac was administered intramuscularly, and sera were collected at 14 days postinfection.
[b]Four HAU of the WT virus was incubated with 2-fold serial dilutions of the indicated sera.
ND, not determined Further experiments were conducted to evaluate the protection efficacy of sciCIV. Female 6-to-8-week-old C57BL/6 mice (n=6) were immunized with the CIV inactivated vaccine (Nobivac; 100 ul intramuscular), or with $1 \times 10^3$ FFU of A/canine/NY/dog23/2009 H3N8 CIV wild-type (WT), $1 \times 10^5$ FFU of sciCIV that was (sciCIV-UV) or was not (sciCIV) exposed to UV light on ice for 20 min; or mock vaccinated with PBS intranasally. Two weeks post-vaccination, mice were challenged with $1 \times 10^5$ FFU of A/canine/NY/dog23/2009 H3N8 CIV WT. To evaluate viral lung replication, mice were sacrificed at days 2 (n=3) and 4 (n=3) post-infection with A/canine/NY/dog23/2009 H3N8 CIV WT and lungs were harvested, homogenized, and used to quantify viral titers by immunofocus assay (FFU/ml) using an anti-NP monoclonal antibody (HB-65). It was observed that sciCIV was protective in inducing immunity against the WT challenge (FIG. 5).

This data demonstrates that sciCIV is protective against influenza homologus A/canine/NY/dog23/2009 H3N8 CIV challenge in a mouse model. Protection efficacy with sciCIV is replication-dependent, which is attributed to both humoral responses and T cells.

Figure 6:
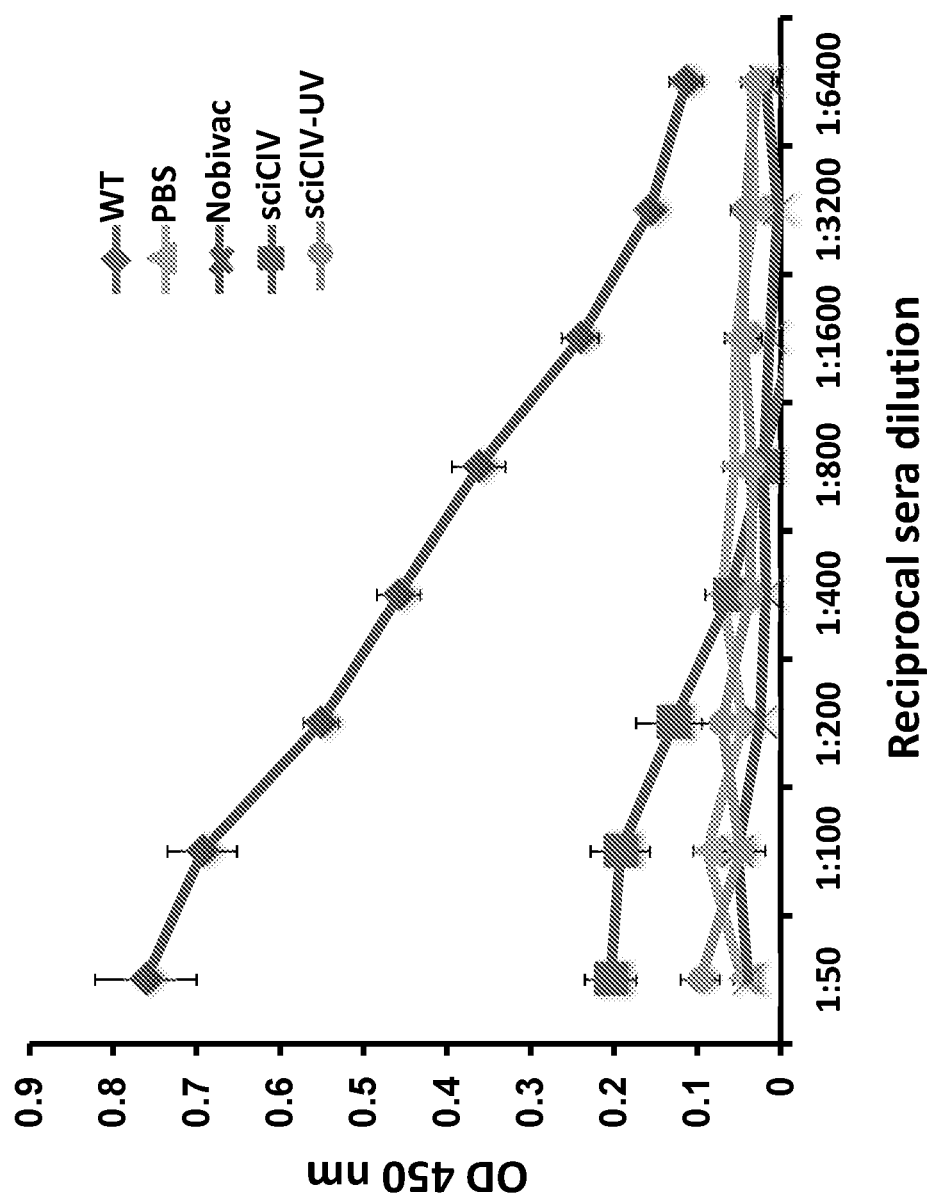
FIG. 6 depicts the results of experiments evaluating the induction of humoral responses by sciCIV vaccination against A/Ca/IL/41915/2015 CIV H3N2: Female 6-to-8-week-old C57BL/6 mice were immunized with the CIV inactivated vaccine (Nobivac; 100 ul intramuscular), or with $1 \times 10^3$ FFU of A/canine/NY/dog23/2009 H3N8 CIV wild-type (WT), $1 \times 10^5$ FFU of sciCIV that was (sciCIV-UV) or was not (sciCIV) exposed to UV light on ice for 20 min; or mock vaccinated with PBS intranasally. At 14 days post-infection, mice were bled and the sera were collected and evaluated by ELISA for IgG antibodies against total influenza virus protein using cell extracts of MDCK cells infected with A/Ca/IL/41915/2015 CIV H3N2. Mock-infected cell extracts were used to evaluate the specificity of the antibody response. OD, optical density. Data represent the means+/−SDs of the results for 4 individual mice.
Figure 7:
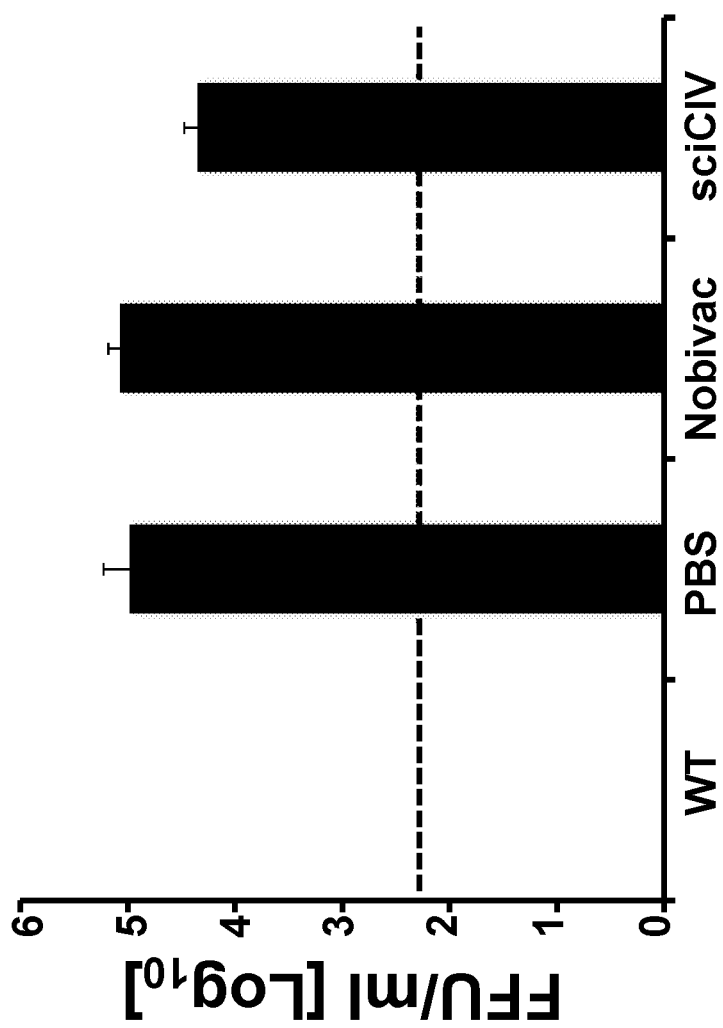
FIG. 7 depicts the results of example experiments evaluating the protection efficacy of sciCIV against A/Ca/IL/41915/2015 CIV H3N2: Female 6-to-8-week-old C57BL/6 mice (n=3) were immunized intranasally with the CIV inactivated vaccine (Nobivac; 100 ul intramuscular), or with $1 \times 10^3$ FFU of A/canine/NY/dog23/2009 H3N8 CIV wild-type (WT), $1 \times 10^5$ FFU of sciCIV or mock vaccinated with PBS intranasally. Two weeks post-vaccination, mice were challenged with $1 \times 10^5$ FFU of CIV H3N2 wild-type (A/Ca/IL/41915/2015). To evaluate viral lung replication, mice were sacrificed at days 3 (n=3) post-challenge and lungs were harvested, homogenized, and used to quantify viral titers by immunofocus assay (FFU/ml) using an anti-NP monoclonal antibody (HB-65). Dotted black lines indicate limit of detection (200 FFU/ml). Data represent the means+/−SDs.

Further experiments were conducted to examine the ability of the H3N8 sciCIV to induce humoral responses against A/Ca/IL/41915/2015 CIV H3N2: Female 6-to-8-week-old C57BL/6 mice were immunized with the CIV inactivated vaccine (Nobivac; 100 ul intramuscular), or with $1\times10^3$ FFU of A/canine/NY/dog23/2009 H3N8 CIV wild-type (WT), $1\times10^5$ FFU of sciCIV that was (sciCIV-UV) or was not (sciCIV) exposed to UV light on ice for 20 min; or mock vaccinated with PBS intranasally. At 14 days post-infection, mice were bled and the sera were collected and evaluated by ELISA for IgG antibodies against total influenza virus protein using cell extracts of MDCK cells infected with A/Ca/IL/41915/2015 CIV H3N2. Mock-infected cell extracts were used to evaluate the specificity of the antibody response. It was observed that the H3N8 sciCIV induced humoral responses against H3N2 CIV (FIG. 6).

Further experiments were conducted to evaluate the protection efficacy of H3N8 sciCIV against A/Ca/IL/41915/2015 CIV H3N2. Female 6-to-8-week-old C57BL/6 mice (n=3) were immunized intranasally with the CIV inactivated vaccine (Nobivac; 100 ul intramuscular), or with $1\times10^3$ FFU of A/canine/NY/dog23/2009 H3N8 CIV wild-type (WT), $1\times10^5$ FFU of sciCIV or mock vaccinated with PBS intranasally. Two weeks post-vaccination, mice were challenged with $1\times10^5$ FFU of CIV H3N2 wild-type (A/Ca/IL/41915/2015). To evaluate viral lung replication, mice were sacrificed at days 3 (n=3) post-challenge and lungs were harvested, homogenized, and used to quantify viral titers by immunofocus assay (FFU/ml) using an anti-NP monoclonal antibody (HB-65). Again, it was observed that H3N8 sciCIV was able to protect against H3N2 CIV.

Thus, the present data demonstrates that sciCIV is able to protect against the newly introduced H3N2 CIV (A/Ca/IL/41915/2015). Altogether, the present studies demonstrate that the present sciCIV approach has potential as safe and broadly protective live attenuated vaccine against CIV.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for preventing canine influenza in a subject, the method comprising administering to the subject an immunological composition comprising a single-cycle infectious canine influenza virus (sciCIV) of the H3N8 subtype of influenza A virus, wherein the sciCIV comprises one or more mutations in segment 4 of the viral genome that results in the lack of expression of HA, wherein the subject does not have canine influenza, and wherein the method induces immunity against influenza A virus subtype H3N2.

2. The method of claim 1, wherein the one or more mutation comprises the deletion of the whole nucleotide sequence encoding HA.

3. The method of claim 1, wherein the immunological composition is administered intranasally, intratracheally, orally, intradermally, intramuscularly, intraperitoneally, intravenously, or subcutaneously.

4. The method of claim 1, wherein the subject is a dog.

5. A method for treating canine influenza in a subject, the method comprising administering to the subject an immunological composition comprising a single-cycle infectious canine influenza virus (sciCIV) of the H3N8 subtype of the influenza A virus, wherein the sciCIV comprises one or more mutations in segment 4 of the viral genome that results in the lack of expression of HA, wherein the subject is infected with influenza A virus subtype H3N2; and wherein the method induces a therapeutic immune response.

6. The method of claim 5, wherein the one or more mutation comprises the deletion of the whole nucleotide sequence encoding HA.

7. The method of claim 5, wherein the immunological composition is administered intranasally, intratracheally, orally, intradermally, intramuscularly, intraperitoneally, intravenously, or subcutaneously.

8. The method of claim 5, wherein the subject is a dog.

* * * * *